United States Patent
Kondo et al.

(10) Patent No.: US 7,572,227 B2
(45) Date of Patent: Aug. 11, 2009

(54) BLOOD PRESSURE MEASURING APPARATUS

(75) Inventors: Akira Kondo, Fujinomiya (JP); Takashi Watanabe, Fujinomiya (JP); Masaru Nakanishi, Fujinomiya (JP); Shuichi Oonishi, Fujinomiya (JP); Hitoshi Ozawa, Fujinomiya (JP); Koichiro Asama, Kanagawa-ken (JP); Shinji Mino, Atsugi (JP)

(73) Assignees: Terumo Kabushiki Kaisha, Shibuya-ku, Tokyo (JP); Nippon Telegraph and Telephone Corporation, Chiyoda-ku, Tokyo (JP)

( * ) Notice: Subject to any disclaimer, the term of this patent is extended or adjusted under 35 U.S.C. 154(b) by 20 days.

(21) Appl. No.: 11/902,350

(22) Filed: Sep. 20, 2007

(65) Prior Publication Data

US 2008/0091112 A1 Apr. 17, 2008

Related U.S. Application Data

(63) Continuation of application No. PCT/JP2006/305953, filed on Mar. 24, 2006.

(30) Foreign Application Priority Data

Apr. 8, 2005 (JP) ............................. 2005-112578

(51) Int. Cl.
*A61B 5/02* (2006.01)
(52) U.S. Cl. .................. 600/485; 600/490; 600/500
(58) Field of Classification Search ................. 600/309, 600/310, 485, 490, 492–496, 500–502
See application file for complete search history.

(56) References Cited

U.S. PATENT DOCUMENTS 4,730,621 A 3/1988 Stott (Continued)

FOREIGN PATENT DOCUMENTS

JP 4-17651 B2 3/1992

(Continued)

OTHER PUBLICATIONS

PCT/ISA/210 and PCT/ISA/237 for PCT/JP12006/305952 dated Apr. 25, 2006.

(Continued)

*Primary Examiner*—Charles A Marmor, II
*Assistant Examiner*—Christian Y Jang
(74) *Attorney, Agent, or Firm*—Buchanan Ingersoll & Rooney PC

(57) ABSTRACT

This invention provides a blood pressure measuring apparatus capable of stably measuring the blood pressure in even the tragus while suppressing the degree of invasion.

An attaching portion (3) of the blood pressure measuring apparatus has an inner cuff (6), an outer cuff (7), and a holding member (10) which holds the inner cuff (6) and outer cuff (7), and the holding member has a "U" shape. The end portions of the holding member (10) where the inner cuff (6) and outer cuff (7) are arranged are almost parallel to each other, and the inner cuff (6) and outer cuff (7) oppose each other. An auxiliary member (80) which comes in contact with a predetermined position of the ear of a person to be measured and increases the attachment stability of the inner cuff (6) and outer cuff (7) at the tragus is attached to the holding member (10).

16 Claims, 26 Drawing Sheets

U.S. PATENT DOCUMENTS

| | | | |
|---|---|---|---|
| 6,575,912 B1 * | 6/2003 | Turcott | 600/485 |
| 2002/0169381 A1 * | 11/2002 | Asada et al. | 600/485 |
| 2004/0054291 A1 * | 3/2004 | Schulz et al. | 600/500 |
| 2005/0049468 A1 * | 3/2005 | Carlson et al. | 600/323 |
| 2005/0141729 A1 * | 6/2005 | Kanzaki et al. | 381/67 |
| 2005/0256386 A1 * | 11/2005 | Chan et al. | 600/335 |

FOREIGN PATENT DOCUMENTS

| | | | |
|---|---|---|---|
| JP | 2005-6906 A | 1/2005 | |
| WO | WO 2005/034742 A1 | 4/2005 | |

OTHER PUBLICATIONS

English-language translations of International Preliminary Report on Patentability (Form PCT/IB/373), Written Opinion (Form PCT/IB/237) and accompanying Transmittal Letter (Form PCT/IB/338), Aug. 21, 2008, IB of WIPO, Geneva, CH.

* cited by examiner

BLOOD PRESSURE MEASURING APPARATUS

TECHNICAL FIELD

The present invention relates to a blood pressure measuring apparatus and, more particularly, to a technique that uses the external ear and its periphery as portions to be measured.

BACKGROUND ART

The blood pressure changes momentarily in accordance with changes in external and internal environments. Therefore, it is ideal to be able to continuously record heart beats one after another. Even though this continuous recording is impossible, however, it is also important to provide health care by measuring the change in blood pressure with time by periodically (intermittently) measuring the blood pressure in a day.

When periodically measuring the blood pressure by the conventional blood pressure measuring apparatus, the blood pressure is measured by winding a cuff on the brachium of a person to be measured. In this case, it is necessary to attach, to the body, a large cuff that covers the brachium and the main body of the blood pressure measuring apparatus connected to the cuff.

When periodically measuring the blood pressure by the blood pressure measuring apparatus, therefore, a person to be measured must live everyday life with the cuff being attached to the brachium and the main body of the blood pressure measuring apparatus connected to the cuff being attached to the body. This largely interferes with everyday life. There is also a burden on the person to be measured; he or she may feel pain because the brachium is pressed whenever the blood pressure is measured.

There is a method that takes this problem into account and measures the pulse wave by attaching a cuff to the earlobe and pressing it (patent reference 1). This method can make the cuff and main body smaller than a sphygmomanometer that measures the blood pressure by attaching a cuff to the brachium, and can also reduce the burden on a person to be measured. Patent reference 1: Japanese Patent Laid-Open No. 2005-6906

DISCLOSURE OF INVENTION

Problems that the Invention is to Solve

Even when measuring the pulse wave or blood pressure in the earlobe, however, it is difficult to stably and accurately measure the blood pressure because the blood vessels in the earlobe are very thin. In particular, the blood vessels in the earlobe shrink when the external temperature lowers, and this makes stable measurement more difficult.

If, therefore, the blood pressure or the like is measured by attaching the cuff to the tragus in which the blood vessels are thicker than those of the earlobe, it is presumably possible to stably measure the blood pressure relatively close to that in the brachium.

Unfortunately, although the cuff can be easily attached to the earlobe because it is soft, relatively large, and largely exposed, the tragus is relatively hard and has a large difference in shape between individuals, so the structure of the earlobe cuff disclosed in patent reference 1 cannot be directly diverted to the tragus. That is, even when the structure of the attaching portion disclosed in patent reference 1 is used, it is difficult to stably obtain the results of blood pressure measurement in the tragus. Also, if the cuff is attached to the tragus by force, the degree of invasion to the person to be measured may increase.

The present invention has been made in consideration of the above situation, and provides a blood pressure measuring apparatus having a cuff attaching structure capable of stably measuring the blood pressure even in the tragus while decreasing the degree of invasion.

Means of Solving the Problems

To solve the above problem, a blood pressure measuring apparatus according to the present invention is characterized by comprising an inner cuff to be inserted into an ear hole, and an outer cuff to be positioned outside a tragus, holding means for holding the inner cuff and the outer cuff, pulse wave detecting means incorporated into at least one of the inner cuff and the outer cuff to detect a pulse wave signal from blood flowing through a blood vessel, pressurizing/depressurizing means for pressurizing and depressurizing the inner cuff and the outer cuff by using a fluid, after the inner cuff and the outer cuff clamp the tragus, a tube connected from the inner cuff and the outer cuff to the pressurizing/depressurizing means to supply the fluid, pressure detecting means connected to the tube to detect pressures of the inner cuff and the outer cuff, and blood pressure measurement control means for measuring a blood pressure value from the pulse wave signal, wherein one end of the holding means is open, end portions of the holding means where the inner cuff and the outer cuff are arranged are substantially parallel, the inner cuff and the outer cuff oppose each other, and an auxiliary member which comes in contact with a predetermined position of an ear of a person to be measured and increases attachment stability of the inner cuff and the outer cuff at the tragus is attached to the holding means.

The auxiliary member protrudes from the holding means, and a length of the protrusion from the holding means is adjustable by a protrusion length adjusting mechanism.

The apparatus further comprises an ear hook which has a tube holding portion which holds the tube connected to the inner cuff and the outer cuff, and guides the tube to the pressurizing/depressurizing means through a back of the ear of the person to be measured. The ear hook and the holding means are independent members except for portions integrated via the tube. Also, the ear hook has a shape portion which presses at least an antihelix of the ear of the person to be measured.

A stopper member which regulates a length to be pulled in a predetermined direction is attached to the tube. The tube holding portion of the ear hook has a plurality of tube holding portions, and the stopper member is attached to a position of a tube holding portion closest to the holding means.

The holding means includes a first holding member which holds the outer cuff and a second holding member which holds the inner cuff, the first holding member is pivotally connected to the second holding member, and when the first holding member is in a steady position without pivoting, the first holding member and an end portion of the second holding member at which the inner cuff is placed are substantially parallel to each other in the holding means, and the inner cuff and the outer cuff oppose each other.

The apparatus further comprises a clamping width adjusting mechanism which adjusts a clamping width between the outer cuff and the inner cuff.

A head turn mechanism attaches at least one of the outer cuff and the inner cuff to the holding means.

Note that a circumferential surface of each of the outer cuff and the inner cuff, except for a contact surface which comes in direct contact with the tragus, is formed into bellows, and that the numbers of steps of the bellows of the outer cuff and the inner cuff are the same.

The sectional shapes of the outer cuff and the inner cuff are different. For example, the sectional shape of the outer cuff is substantially a circle, and the sectional shape of the inner cuff is substantially an ellipse or oval.

Also, a blood pressure measuring apparatus according to the present invention is characterized by comprising an inner cuff to be inserted into an ear hole, and an outer cuff to be positioned outside a tragus, holding means for holding the inner cuff and the outer cuff, pulse wave detecting means incorporated into at least one of the inner cuff and the outer cuff to detect a pulse wave signal obtained by light from blood flowing through a blood vessel, pressurizing/depressurizing means for pressurizing and depressurizing the inner cuff and the outer cuff by using a fluid, after the inner cuff and the outer cuff clamp the tragus, a tube connected from the inner cuff and the outer cuff to the pressurizing/depressurizing means to supply the fluid, pressure detecting means connected to the tube to detect pressures of the inner cuff and the outer cuff, and blood pressure measurement control means for measuring a blood pressure value from the pulse wave signal, wherein the inner cuff and the outer cuff oppose each other, and a cuff which receives the light has a light-shielding layer which prevents disturbance light.

Furthermore, a blood pressure measuring apparatus according to the present invention is characterized by comprising an inner cuff to be inserted into an ear hole, and an outer cuff to be positioned outside a tragus, holding means for holding the inner cuff and the outer cuff, pulse wave detecting means incorporated into at least one of the inner cuff and the outer cuff to detect a pulse wave signal obtained by light from blood flowing through a blood vessel, pressurizing/depressurizing means for pressurizing and depressurizing the inner cuff and the outer cuff by using a fluid, after the inner cuff and the outer cuff clamp the tragus, a tube connected from the inner cuff and the outer cuff to the pressurizing/depressurizing means to supply the fluid, pressure detecting means connected to the tube to detect pressures of the inner cuff and the outer cuff, and blood pressure measurement control means for measuring a blood pressure value from the pulse wave signal, wherein the inner cuff and the outer cuff oppose each other, and a thickness of a lid portion of each of the inner cuff and the outer cuff is made larger than a thickness of a cylindrical portion.

Other features of the present invention will be apparent below from the best mode for carrying out the invention and the accompanying drawings.

EFFECTS OF THE INVENTION

The arrangement of the present invention can increase the stability of cuff attachment. It is also possible to evenly bring the cuffs into contact with the inner and outer surfaces of the tragus in a flat state, and the cuffs can accurately measure the blood pressure while maintaining positions well corresponding to an individual difference in tragus shape.

Other features and advantages of the present invention will be apparent from the following explanation taken in conjunction with the accompanying drawings. Note that the same reference numerals denote similar arrangements or the same arrangements in the accompanying drawings.

BRIEF DESCRIPTION OF DRAWINGS

The accompanying drawings are included in the specification, constitute part of the specification, illustrate embodiments of the present invention, and are used to explain the principle of the present invention together with the description.

Figure 1:
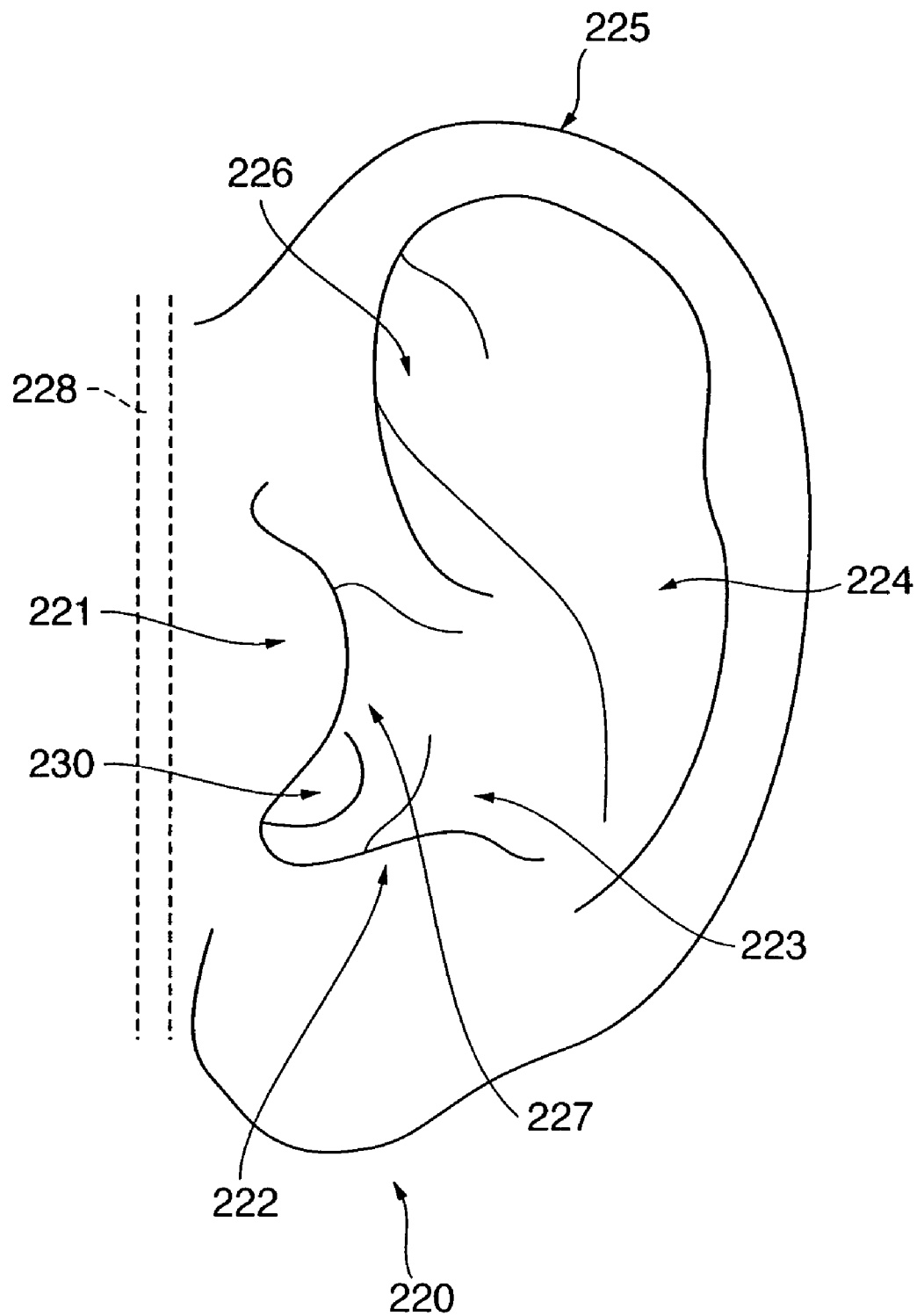
FIG. 1 is a view showing the structure of the ear.
Figure 2:
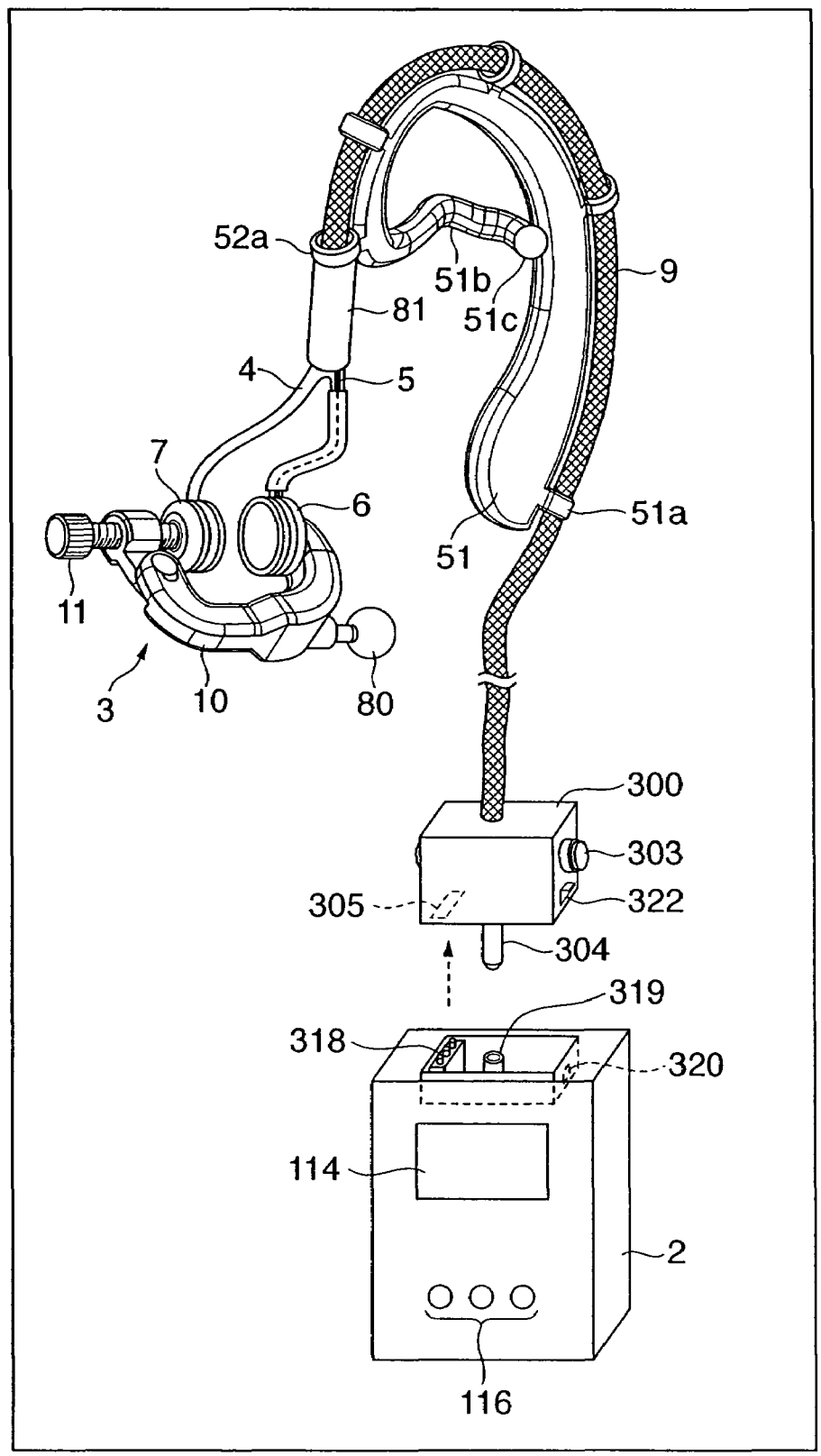
FIG. 2 is a view showing the outer appearance of a blood pressure measuring apparatus according to the present invention.
Figure 11:
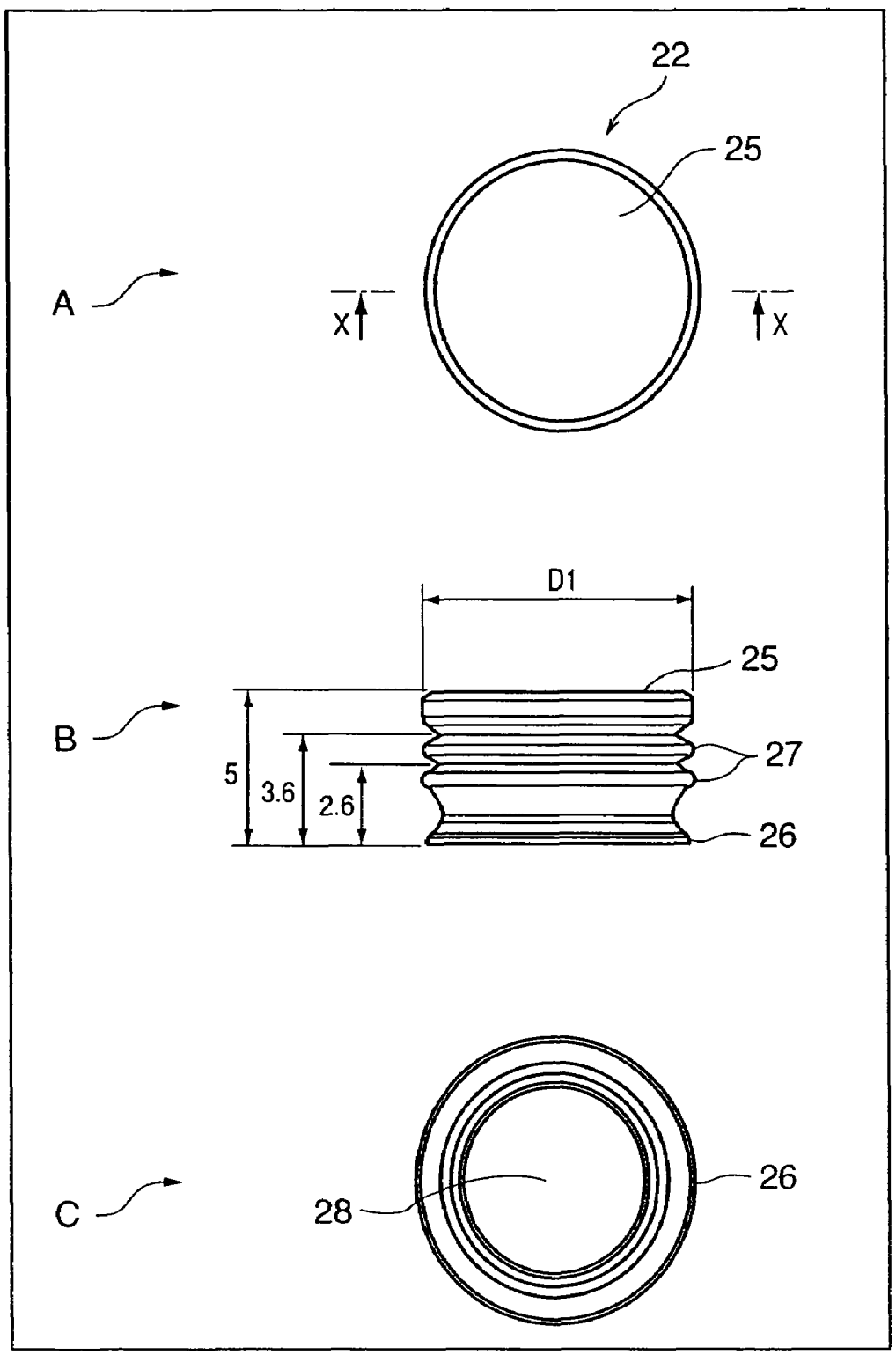
Figure 12:
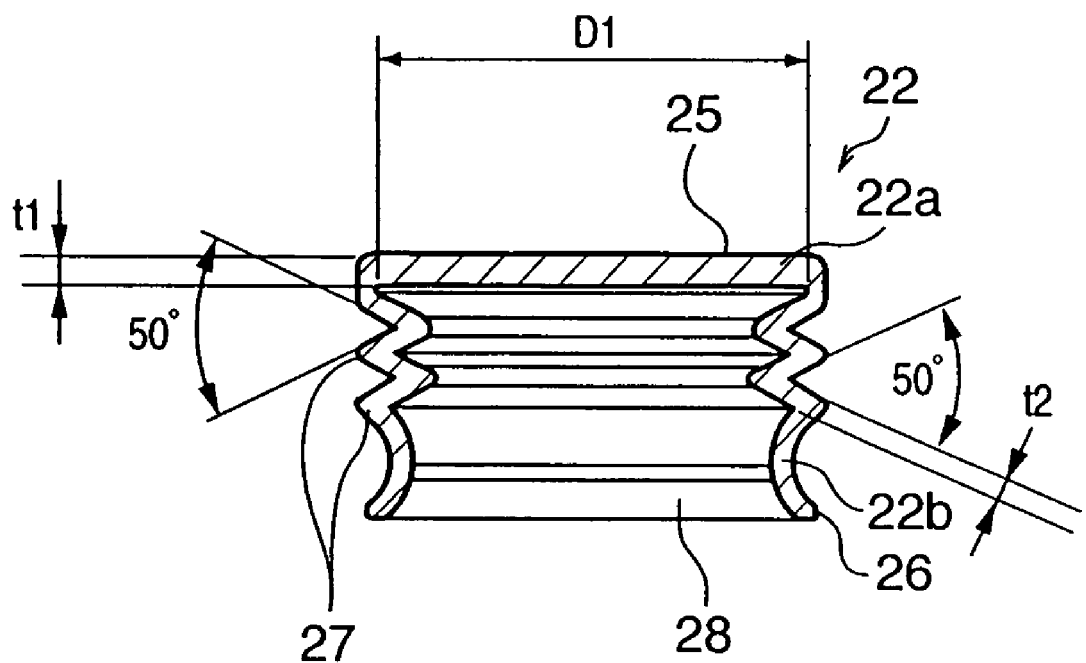
Figure 13:
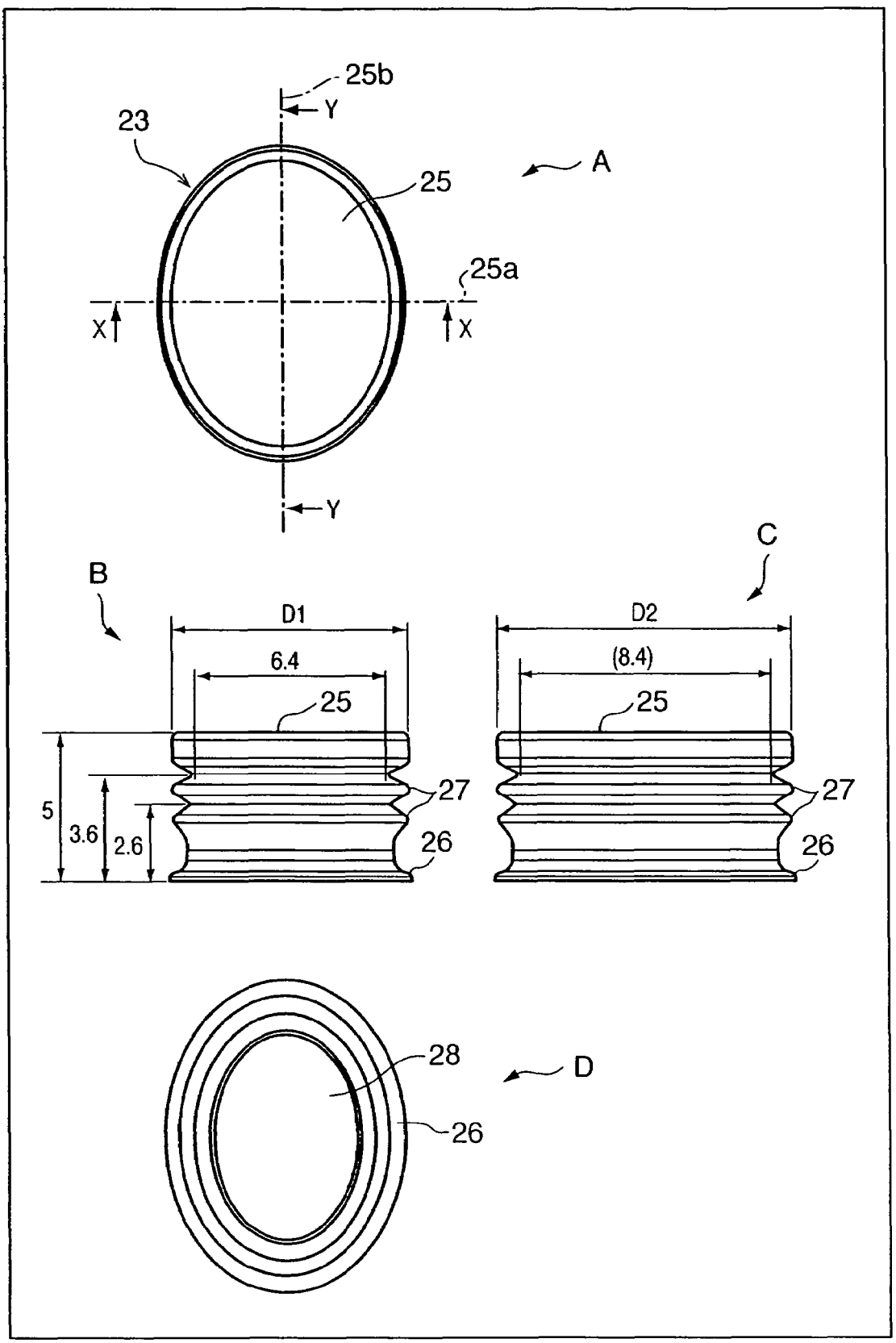
Figure 14:
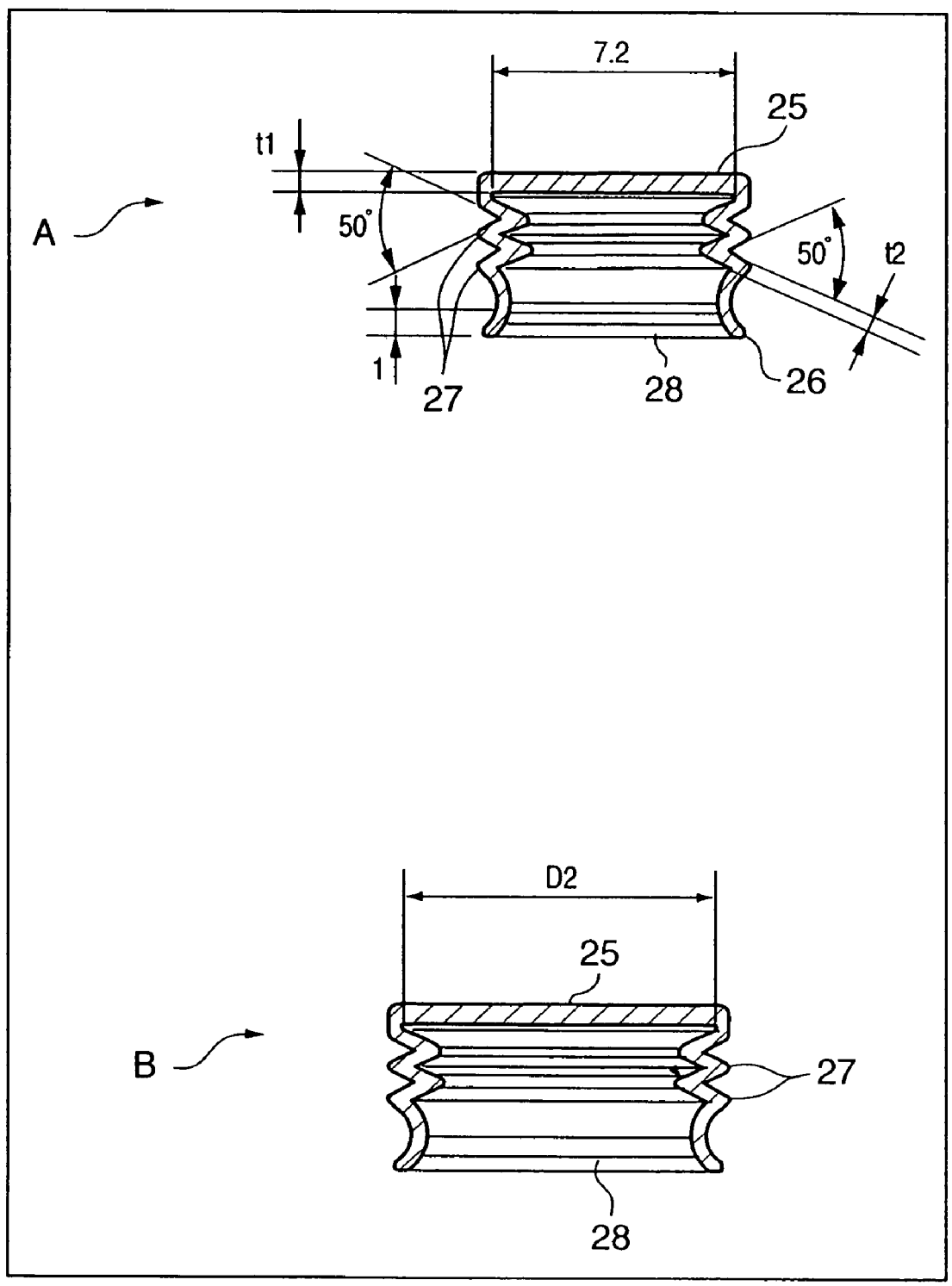
Figure 15:
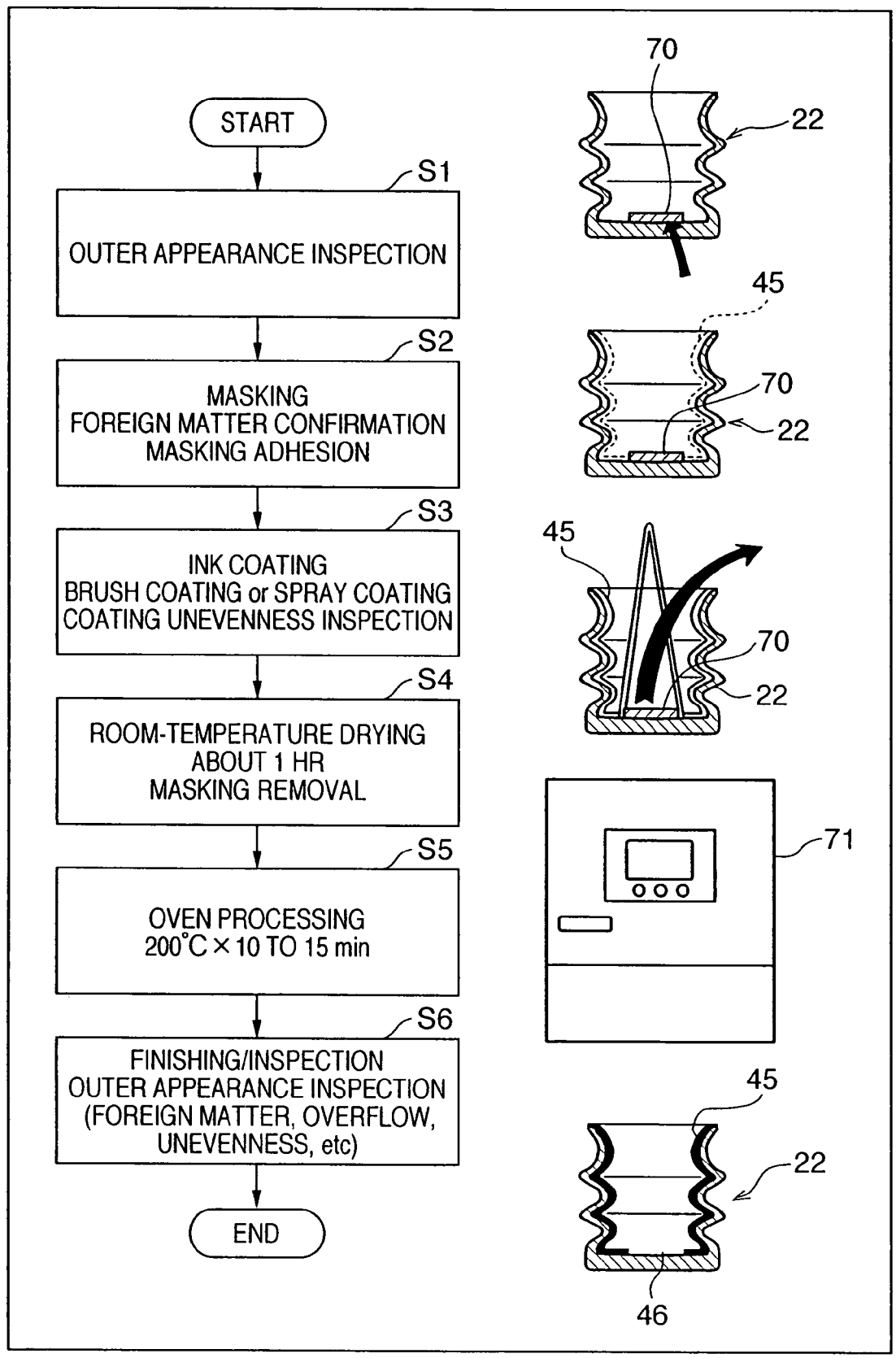
Figure 16:
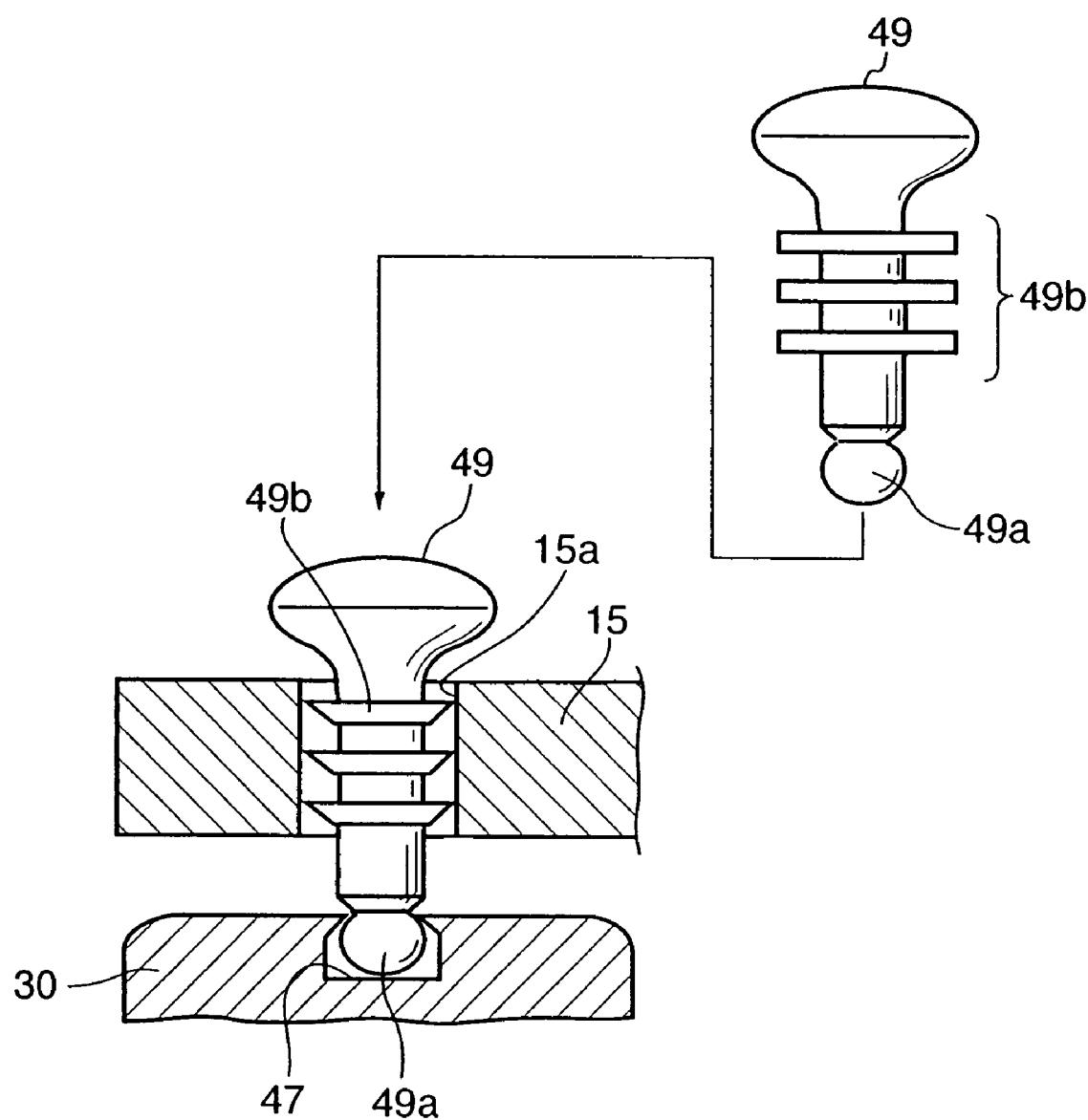
Figure 17:
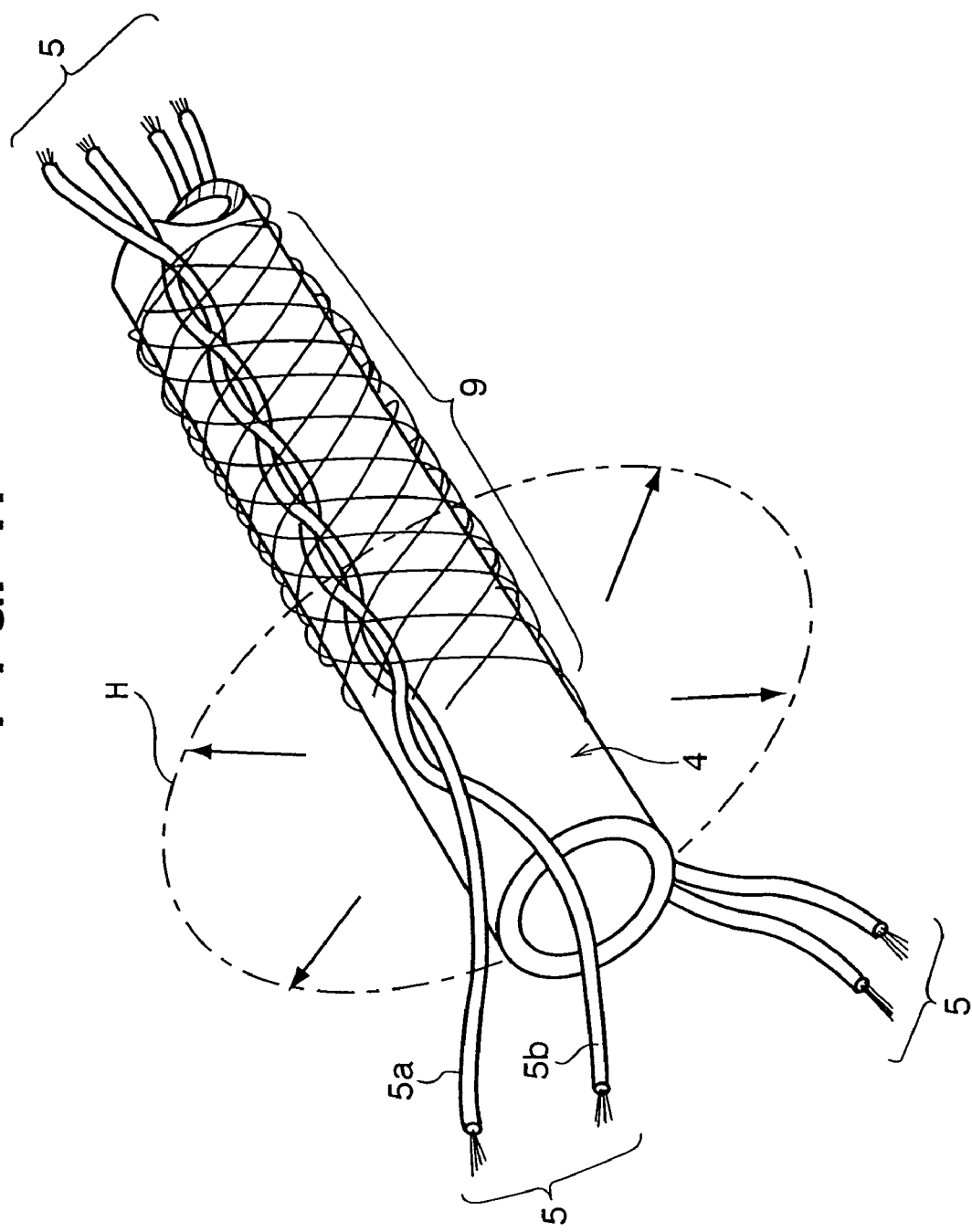
Figure 18:
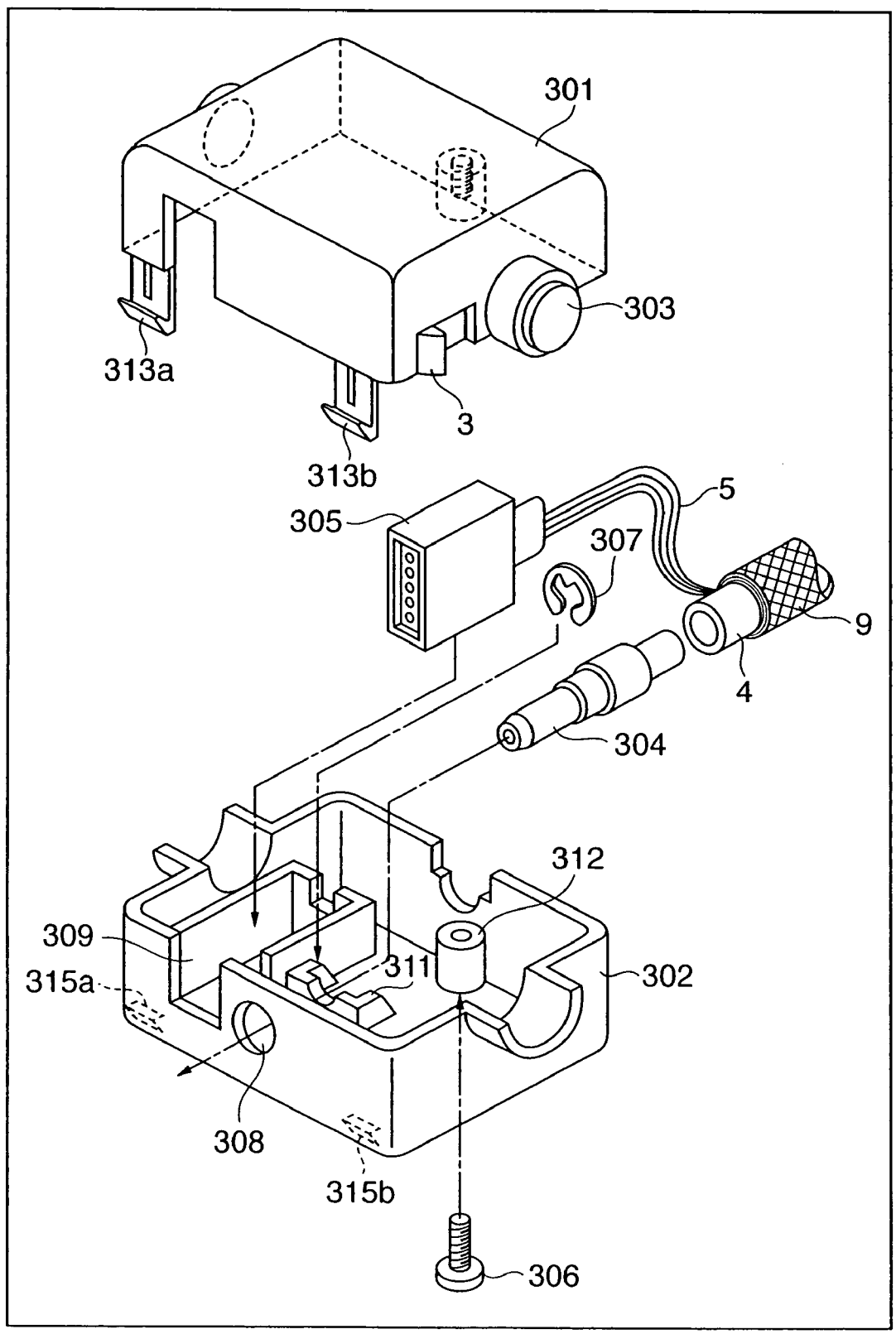
Figure 19:
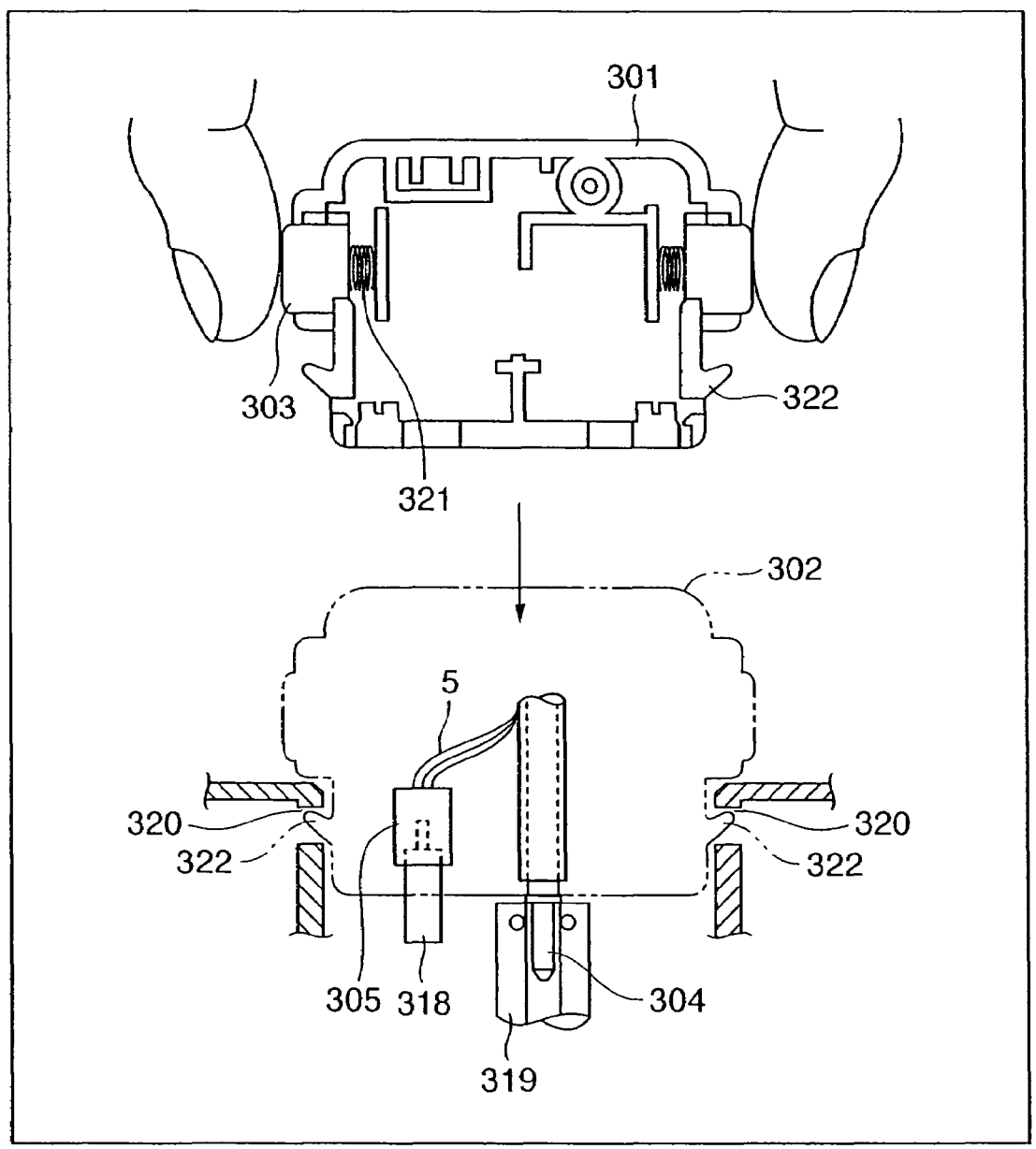
Figure 20:
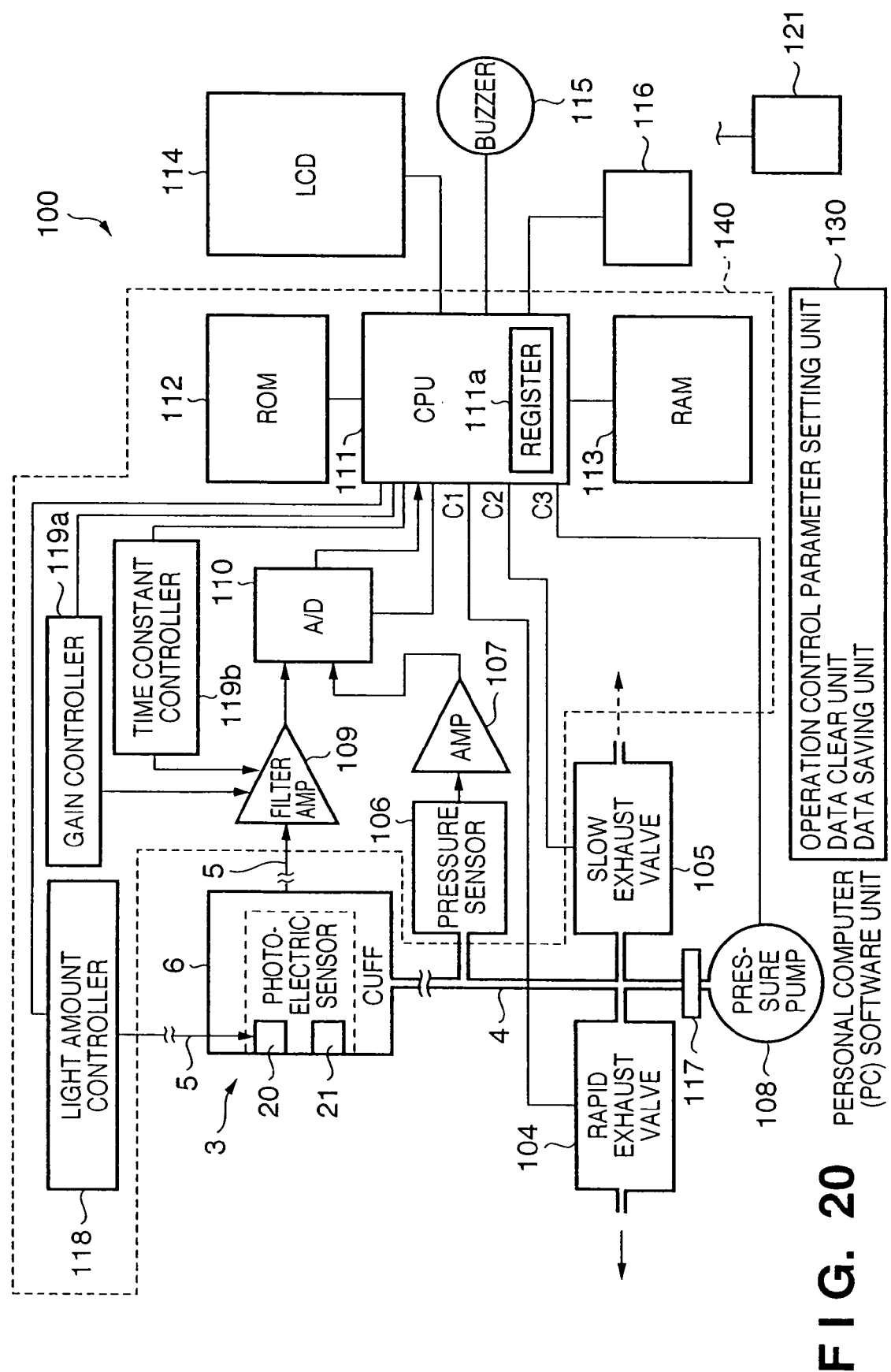
Figure 21:
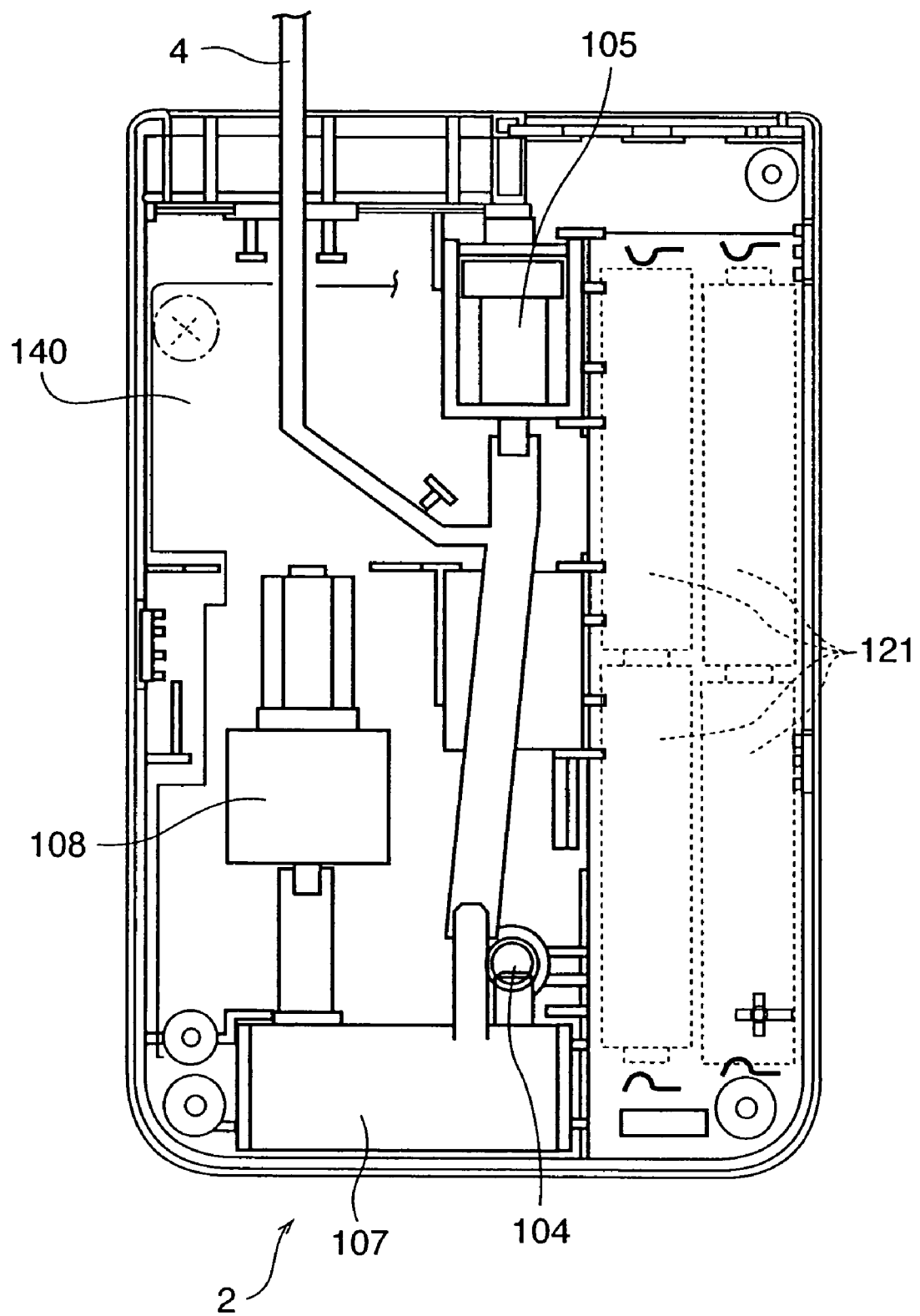
Figure 22A:
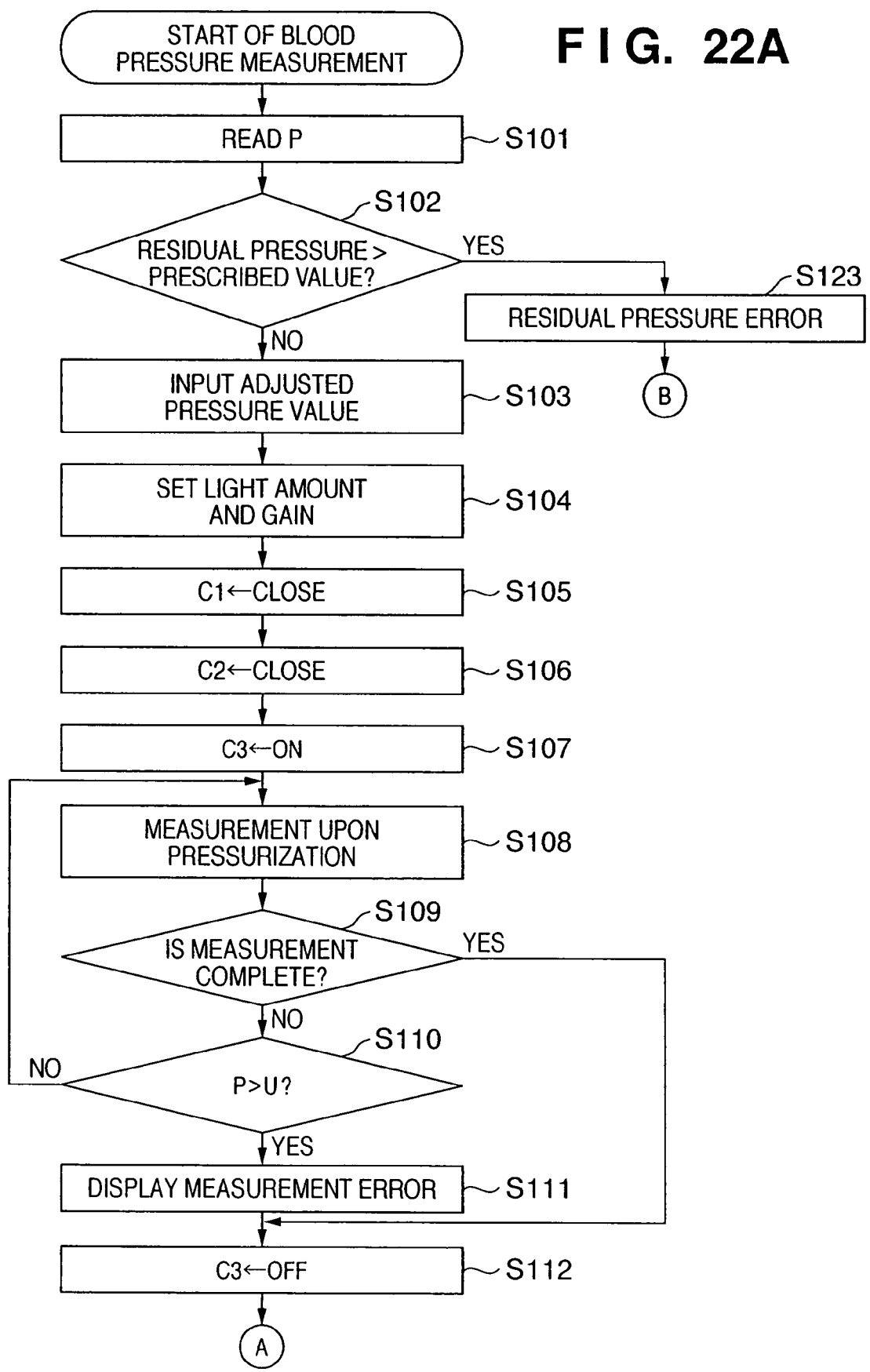
Figure 22B:
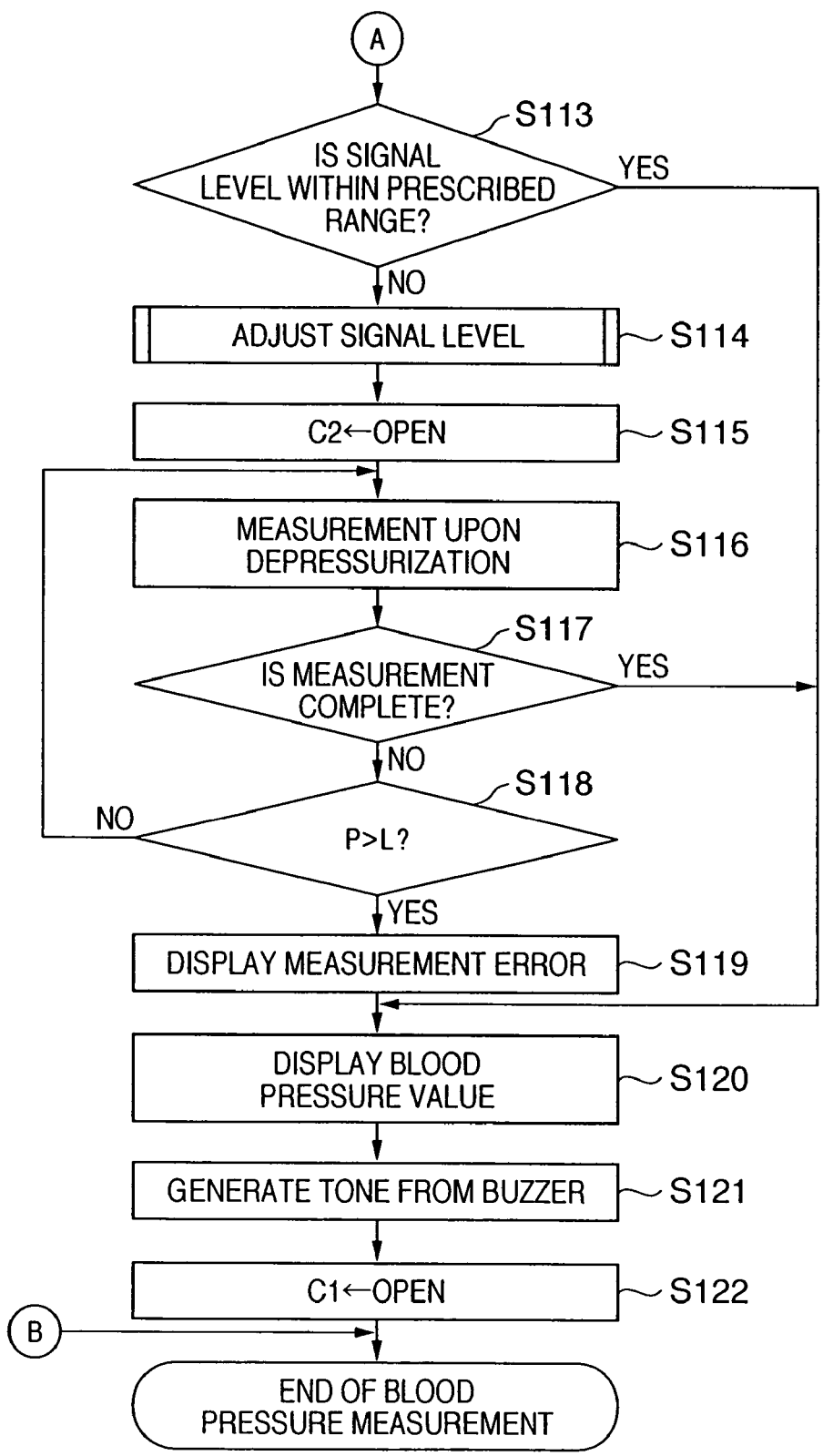
Figure 23:
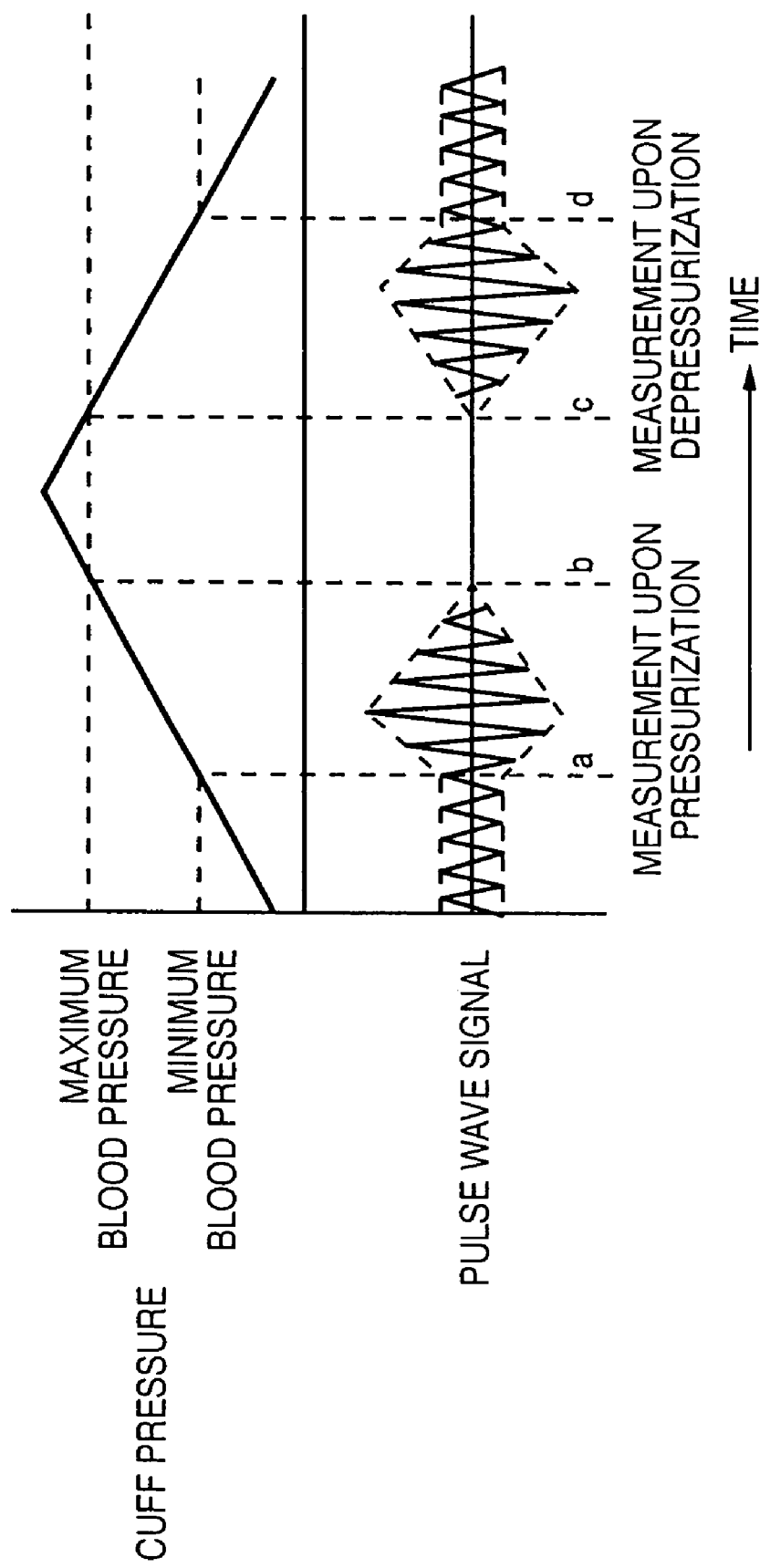
Figure 24:
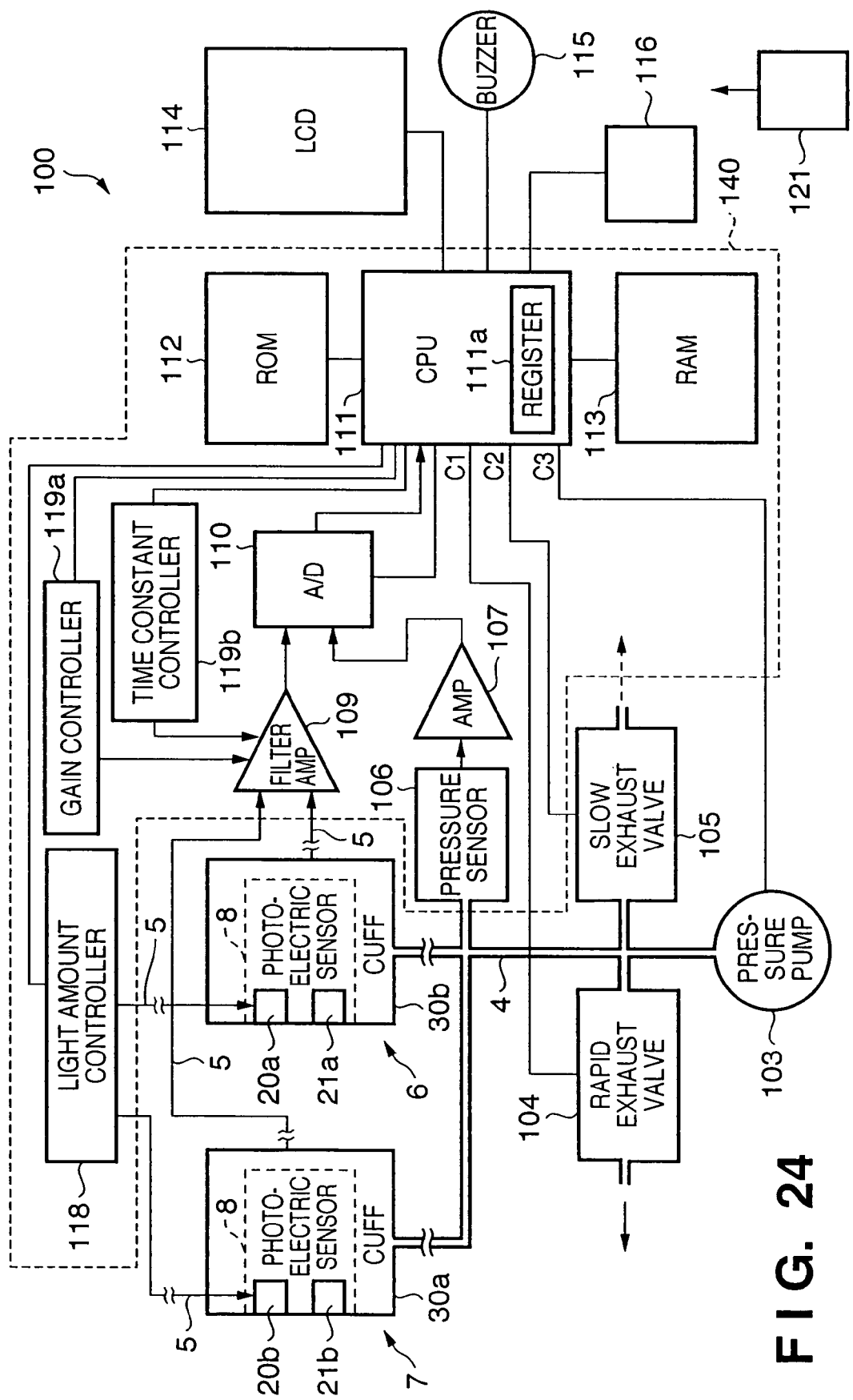
Figure 25:
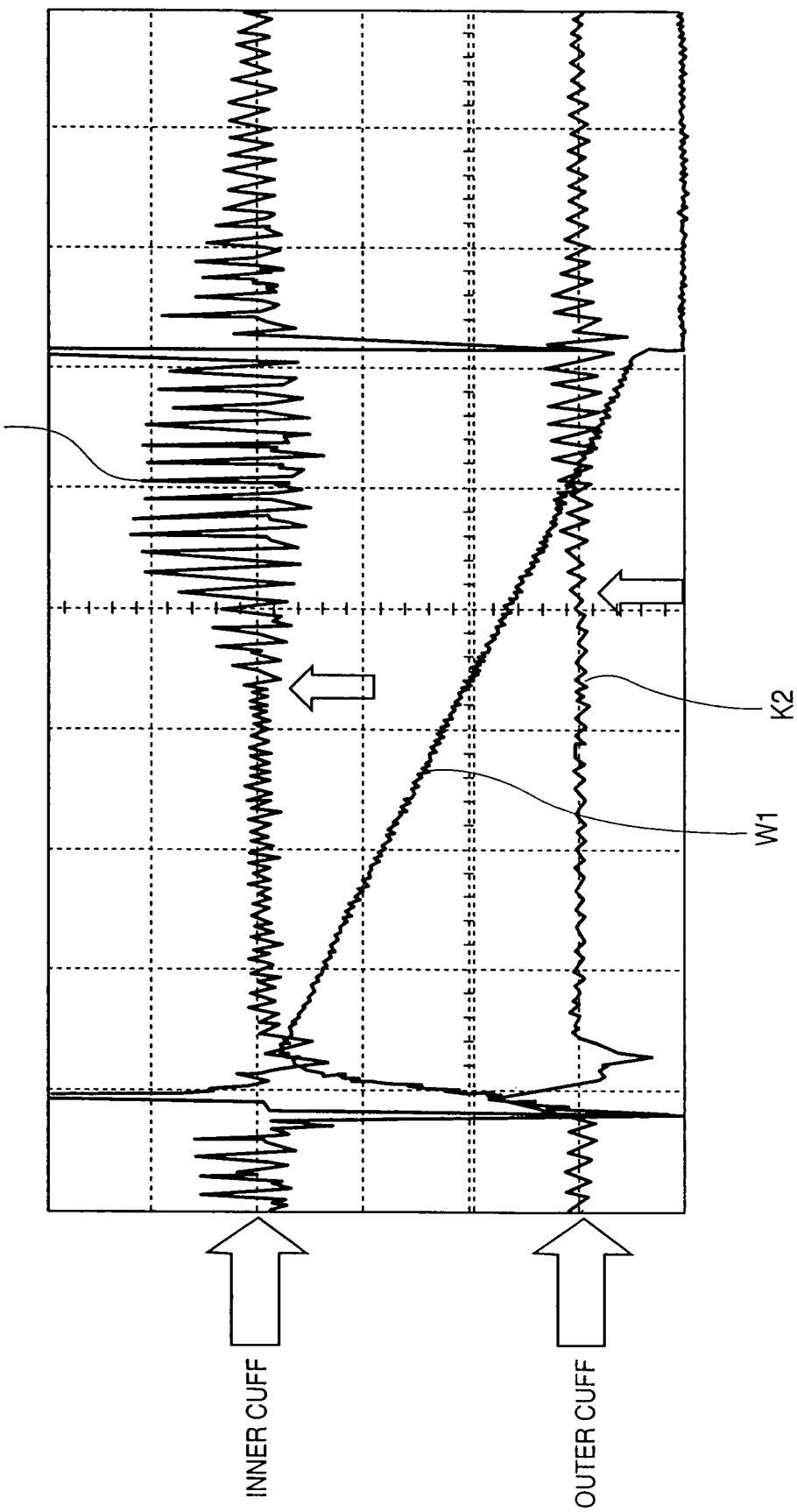

A of FIG. 11 is a plan view of a cuff bladder 22, B of FIG. 11 is a front view of the cuff bladder, and C of FIG. 11 is a bottom view of the cuff bladder;

FIG. 12 is a sectional view taken along a line X-X in FIG. 11A;

A of FIG. 13 is a plan view of a cuff bladder 23, B of FIG. 13 is a front view of the cuff bladder, C of FIG. 13 is a right side view of the cuff bladder, and D of FIG. 13 is a bottom view of the cuff bladder;

A of FIG. 14 is a sectional view taken along a line X-X in A of FIG. 13, and B of FIG. 14 is a sectional view taken along a line Y-Y in A of FIG. 13;

FIG. 15 is a view showing printing steps of forming a light-shielding layer in the interior of the cuff bladder 22, together with the central sectional views of the cuff bladder 22;

FIG. 16 is a sectional view showing the main parts of the cuff assembly formed to have a degree of freedom at the end portion of a brushing bush of a unidirectional moving member;

FIG. 17 is an outer appearance perspective view showing the way cables and a tube are integrated;

FIG. 18 is a view showing the structure of a connecting portion 300;

FIG. 19 is a view for explaining the way the connecting portion 300 is attached;

FIG. 20 is a block diagram showing an example of the configuration of the blood pressure measuring apparatus shown in FIG. 1;

FIG. 21 is a view showing the layout of parts of an apparatus main body 2 shown in FIG. 2;

FIG. 22A is a flowchart for explaining the operation of the blood pressure measuring apparatus;

FIG. 22B is a flowchart for explaining the operation of the blood pressure measuring apparatus;

FIG. 23 is a waveform diagram of blood pressure measurement;

FIG. 24 is a block diagram showing an example of the configuration of a blood pressure measuring apparatus according to another embodiment; and FIG. 25 is a waveform diagram showing the results of blood pressure measurement performed by simultaneous measurement by the inner and outer cuffs.

BEST MODE FOR CARRYING OUT THE INVENTION

A blood pressure measuring apparatus of a preferred embodiment according to the present invention will be explained below with reference to the accompanying drawings.

<Structure of Auricle>

The blood pressure measuring apparatus according to this embodiment uses the tragus as an appropriate portion of the auricle as a portion to be measured. The structure of the auricle will be explained first.

FIG. 1 is a view showing the names of portions of the auricle (ear). An auricle 220 shown in FIG. 1 has a tragus 221, antitragus 222, auricular concha 223, antihelix 224, helix 225, antihelix crura 226, auricular concha cavity 227, and ear hole 230. In this embodiment, a pair of attaching portions (made up of, e.g., an inner cuff assembly 6 and outer cuff assembly 7) to be described later are attached so as to clamp the tragus 221.

<Blood Pressure Measuring apparatus Outer Appearance>

FIG. 2 is a view showing the whole outer appearance of the blood pressure measuring apparatus according to this embodiment. This blood pressure measuring apparatus generally comprises a main body 2 that executes a blood pressure measurement operation, an attaching portion 3 that is attached to the tragus 221 of the auricle of a person to be measured, an ear hook 51 that stabilizes attachment of the attaching portion 3, and a connecting portion 300 that connects the main body 2 to a tube 4 and cables 5. The arrangements of the individual parts will be described later, so they will be briefly explained below.

The attaching portion 3 comprises a holding member 10, the inner cuff assembly 6 and outer cuff assembly 7 attached to the holding member 10, a clamping width adjusting screw 11 for adjusting the clamping width between the inner cuff and outer cuff, and an attachment stabilizing member 80.

The ear hook 51 has a shape similar to, e.g., the end piece of an eyeglass frame, and comprises a plurality of tube holding portions 52a in which the tube 4 and cables 5 covered with a covering member 9 are inserted, and a shape portion 51b. An ear hook stabilizing member 51c is formed at the distal end of the shape portion 51b.

The connecting portion 300 connects the tube 4 and cables 5 to the main body 2, and is detachable. The connecting portion 300 is inserted into the main body 2 until locking portions 322 of the connecting portion 300 are locked in locking holes 320 of the main body 2. Consequently, a male connector 318 of the main body 2 is fitted in a female connector 305 of the connecting portion 300, and a tube plug 304 of the connecting portion 300 is fitted in a tube plug hole 319 of the main body 2. The user can remove the connecting portion 300 from the main body 2 by unlocking the locking portions 322 from the locking holes 320 by pressing detaching buttons 303, and pulling out the connecting portion 300 from the main body 2.

The tube 4 and cables 5 are covered with the covering member 9, and inserted into the tube holding portions 51a of the ear hook 51. A stopper member 81 regulates the length by which the tube 4 and cables 5 are pulled toward the main body 2. On the other hand, this embodiment does not regulate the length by which these components are pulled toward the attaching portion 3. However, it is also possible to regulate the length of the tube 4 from the ear hook 51 to the attaching portion 3 by forming stopper members on the two sides of the last tube holding portion 51a of the ear hook 51. The tube 4 branches into two tubes near the attaching portion; one tube is connected together with the cables 5 to the inner cuff assembly 6, and the other tube is connected to the outer cuff assembly 7.

<Cuff Attachment Outer Appearance>

Figure 3:
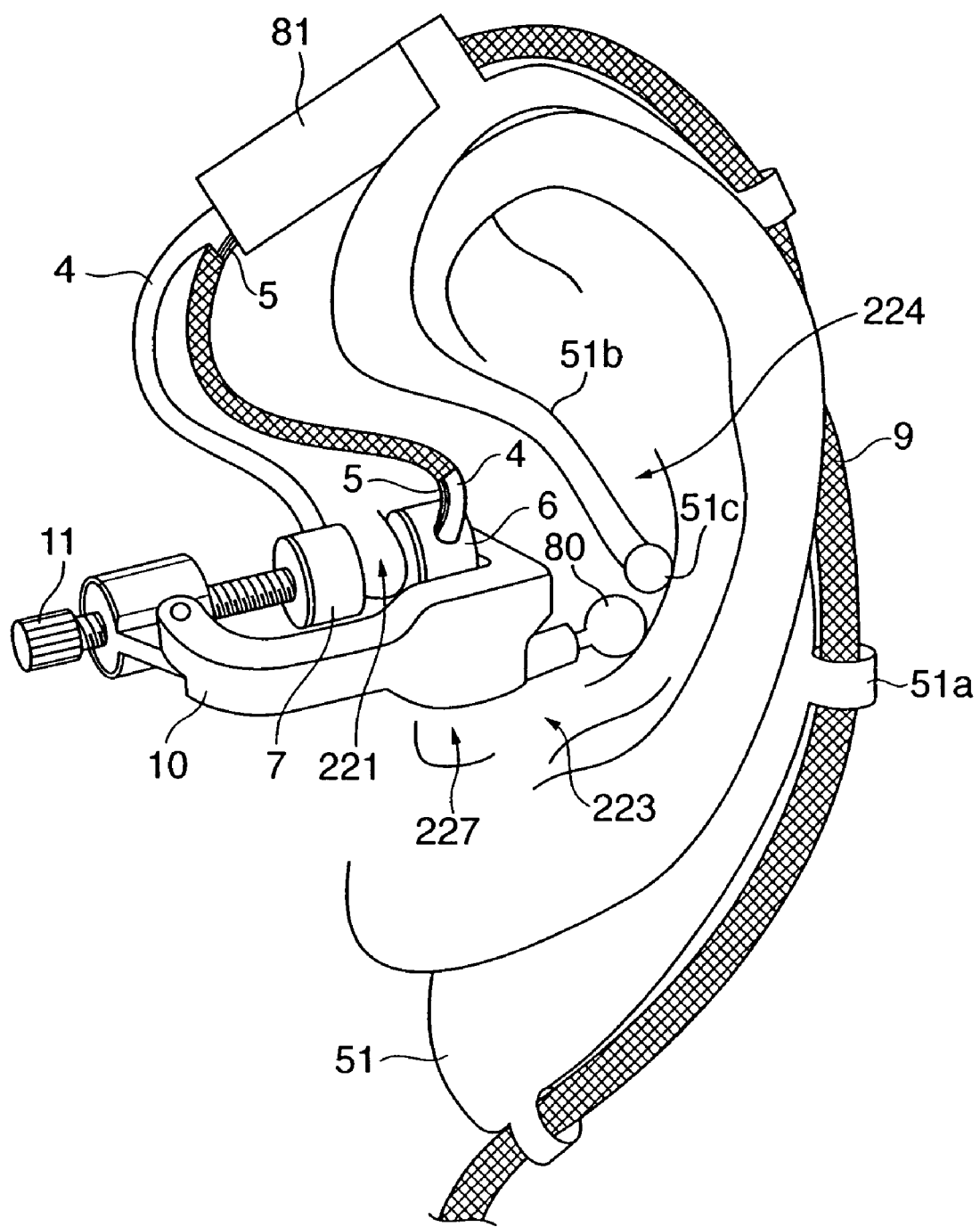
FIG. 3 is an outer appearance perspective view showing the state in which the blood pressure measuring apparatus according to the present invention is used for the auricle.

FIG. 3 is a view showing the way the attaching portion 3 of the blood pressure measuring apparatus according to this embodiment is attached to the tragus 221.

The inner cuff assembly 6 and outer cuff assembly 7 are attached to the upper and lower ends of the "U"-shaped holding member 10. Therefore, the inner cuff assembly 6 and outer cuff assembly 7 oppose each other. The width between the inner cuff assembly 6 and outer cuff assembly 7 can be adjusted by the clamping width adjusting screw 11. When attaching the attaching portion 3 to the tragus 221, therefore, the inner cuff assembly 6 is inserted into the auricular concha cavity 227 by making the width between the two cuffs slightly larger than the thickness of the tragus 221, and fixing the attaching portion 3 to the tragus 221 by tightening the clamping width adjusting screw 11.

Also, the attaching portion 3 has the attachment stabilizing member 80. The distal end portion of the attachment stabilizing member 80 has, e.g., a spherical shape, and comes into contact with the antihelix to increase the stability when the attaching portion 3 is attached to the tragus 221. The attachment stabilizing member 80 has a screw thread, and the length of protrusion of the attachment stabilizing member 80 can be adjusted by threadably engaging this screw thread with a screw hole (not shown) of the holding member 10. This makes it possible to cope with an individual difference of each person to be measured, and more stably attach the attaching portion 3.

The ear hook 51 is attached to the ear as shown in FIG. 3. When the ear hook 51 is attached to the ear, the shape portion 51b extends from the antihelix crura 226 to the antihelix 224 shown in FIG. 1. In the state in which the ear hook 51 is attached to the ear, the distal end portion 51c of the shape portion 51b is positioned near the attachment stabilizing member 80 of the attaching portion 3 in the antihelix 224. As shown in FIG. 3, the tube 4 and cables 5 covered with the covering member 9 are passed behind the ear as they are held by the tube holding portions 51a, and connected to the main body 2. Accordingly, the tube 4 and cables 5 do not interfere with attachment, and do not give trouble to the person to be measured during attachment, so blood pressure measurement can be comfortably executed. The attachment stabilizing member 80 may also be selected from a plurality of members different in size. The holding member 10 must have strength such as shock resistance although it is small in size and light in weight and has a relatively small wall thickness. Therefore, polyphenylene sulfide (PPS) resin or the like is preferably used.

Figure 4:
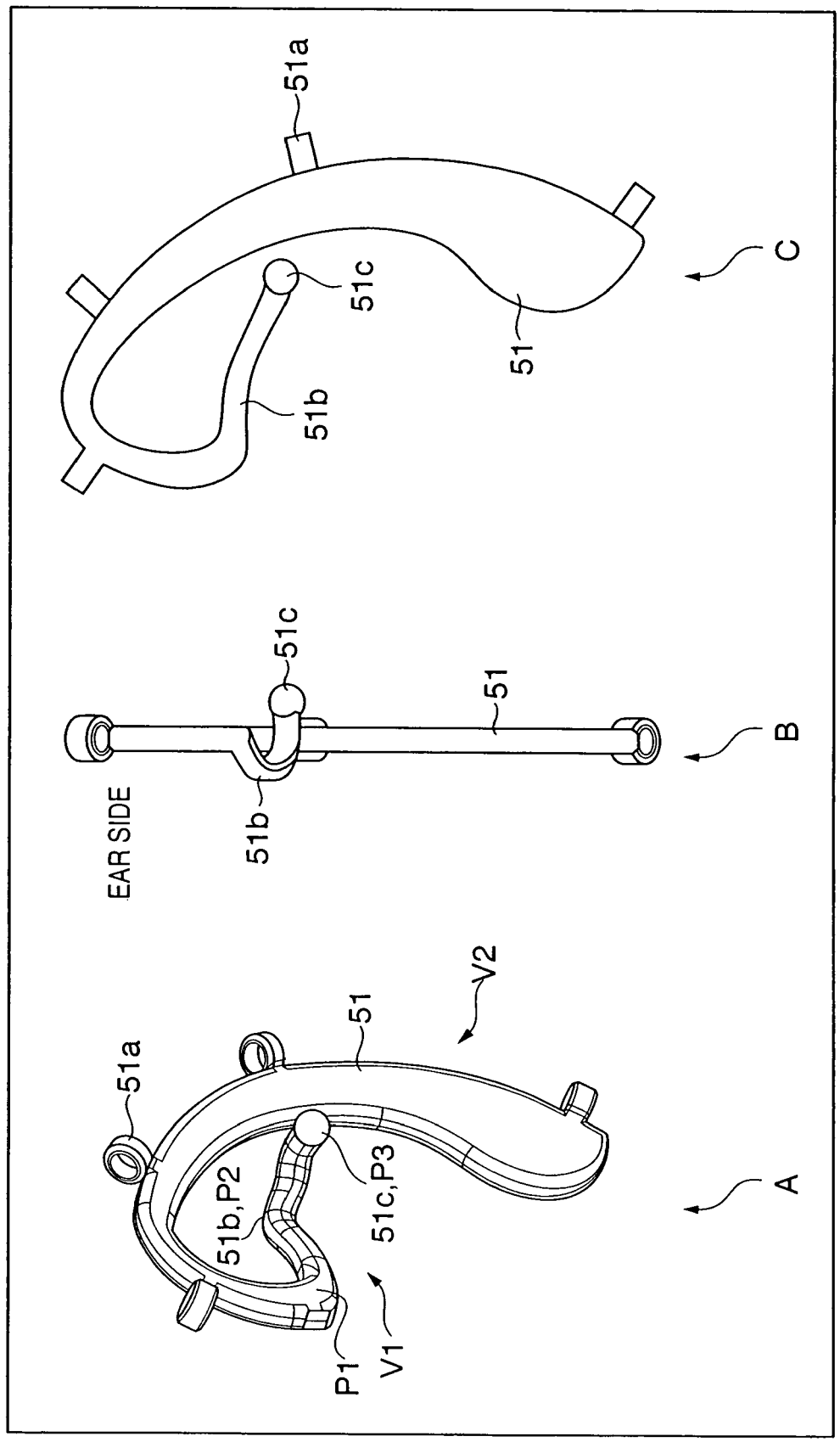
FIG. 4 is a view for explaining the shape of an ear hook 51.

FIG. 4 shows the structure of the ear hook 51. As shown in A of FIG. 4 and as described above, the ear hook 51 has a shape similar to, e.g., the end piece of an eyeglass frame. Also, the ear hook 51 comprises the tube holding portions 51a, the shape portion 51b, and the distal end portion 51c that is formed at the distal end of the shape portion 51b, and stabilizes the attachment of the ear hook. B of FIG. 4 is a view in which the ear hook 51 is viewed in a direction V1, and C of FIG. 4 is a view in which the ear hook S1 is viewed in a direction V2.

B of FIG. 4 well illustrates the feature of the ear hook 51, i.e., the shape of the shape portion 51*b*. The shape portion 51*b* curves from a point P1 to a point P2 of the ear hook 51 so as to come close to the ear. Also, the shape portion 51*b* curves from the point P2 to a point P3 (the distal end portion 51*c*) so as to move away from the ear. Since the shape portion 51*b* has this shape, that portion of the shape portion 51*b* which curves toward the ear matches the curved ear shape from the antihelix crura 226 to the antihelix 224 shown in FIG. 1. This shape of the shape portion 51*b* allows the person to be measured to feel a good sense of fitting. Note that the ear hook 51 is explained as a part for the left ear in this embodiment, but it is of course also possible to provide the ear hook 51 as a part for the right ear. In this case, the shape portion 51*b* has a curve opposite to that described above.

The attaching portion 3 thus attached is connected to the apparatus main body 2 by the tube 4 and cables 5. The tube 4 is used to supply air when pressurizing the cuffs, and exhaust air from the cuffs when depressurizing them. The cables 5 are signal lines for exchanging signals for executing control operations for photoelectric pulse wave blood pressure measurement to be described later, between light-emitting and light-receiving elements to be described later and the apparatus main body 2.

Note that the apparatus main body 2 may also be put into a breast pocket of the person to be measured, or accommodated into a case attached to the waist of the person to be measured.

<Arrangement of Attaching Portion 3>

Figure 5:
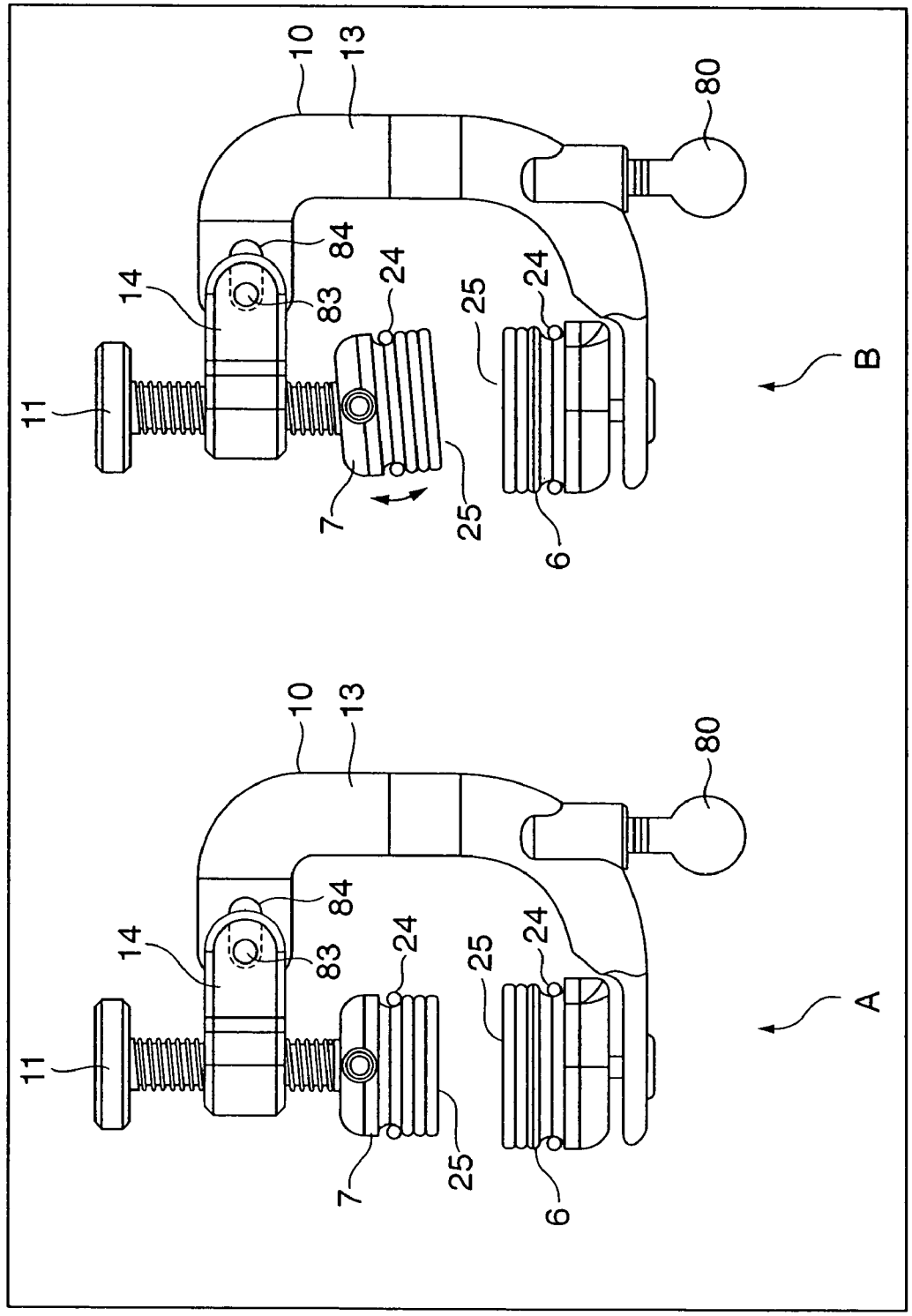
FIG. 5 is a view showing the basic arrangement (A of FIG. 5) and the head turn state (B of FIG. 5) of an attaching portion 3.

FIG. 5 shows the outer appearance of the attaching portion 3. The attaching portion 3 generally comprises the holding member 10, inner cuff assembly 6, outer cuff assembly 7, and clamping width adjusting screw 11 (clamping width adjusting mechanism).

As shown in A of FIG. 5, the holding member 10 has a "U" shape as a whole, and comprises a first holding member 13 to which the outer cuff assembly 7 is attached, and a second holding member 14 to which the inner cuff assembly 6 is attached. The "U" shape means that only one end of the holding member 10 is an open end, and that portions (the upper and lower end portions of the holding member 10) of the first holding member 13 and second holding member 14 where the inner cuff assembly 6 is placed in a normal setting state shown in A of FIG. 5 are almost parallel to each other.

Also, a screw hole for the clamping width adjusting screw 11 is formed near the end portion of the first holding member to which the outer cuff assembly 7 is attached. The outer cuff assembly 7 is attached to the distal end of the clamping width adjusting screw 11. Since the holding member 10 is constructed as described above, the inner cuff assembly 6 and outer cuff assembly 7 oppose each other. The clamping width decreases when the clamping width adjusting screw 11 is rotated clockwise, and increases when the clamping width adjusting screw 11 is rotated counterclockwise.

As shown in A of FIG. 5, the first holding member 13 has the attachment stabilizing member 80. As described previously, the attachment stabilizing member 80 threadably engages with the screw hole (not shown) of the first holding member 13, so the length can be adjusted by tightening or loosening the attachment stabilizing member 80. Note that when the distal end portion of the attachment stabilizing portion 80 is made of a relatively soft material such as polyurethane, it is possible to reduce the physical and psychological burdens on the user when the antihelix 224 and/or the auricular concha 223 and its periphery of the ear are pressed.

Note that the attachment stabilizing member 80 is detachable, and hence can be replaced with an attachment stabilizing member made of another material or with a member having a distal-end spherical portion of a different size (e.g., a small spherical portion for children).

The outer cuff assembly 7 of the attaching portion 3 according to this embodiment is not always fixed and opposed to the inner cuff assembly 6. To flexibly cope with various shapes of the tragi 221, as shown in B of FIG. 5, the outer cuff assembly 7 is attached to the clamping width adjusting screw 11 by using a head turn mechanism so that the outer cuff assembly 7 turns its head. Similarly, the inner cuff assembly 6 is mounted on the end portion of the first holding member 13 by using a head turn mechanism. As described above, the two cuff assemblies can freely adapt to the shape of the tragus 221. Note that this head turn mechanism will be described later.

Figure 6:
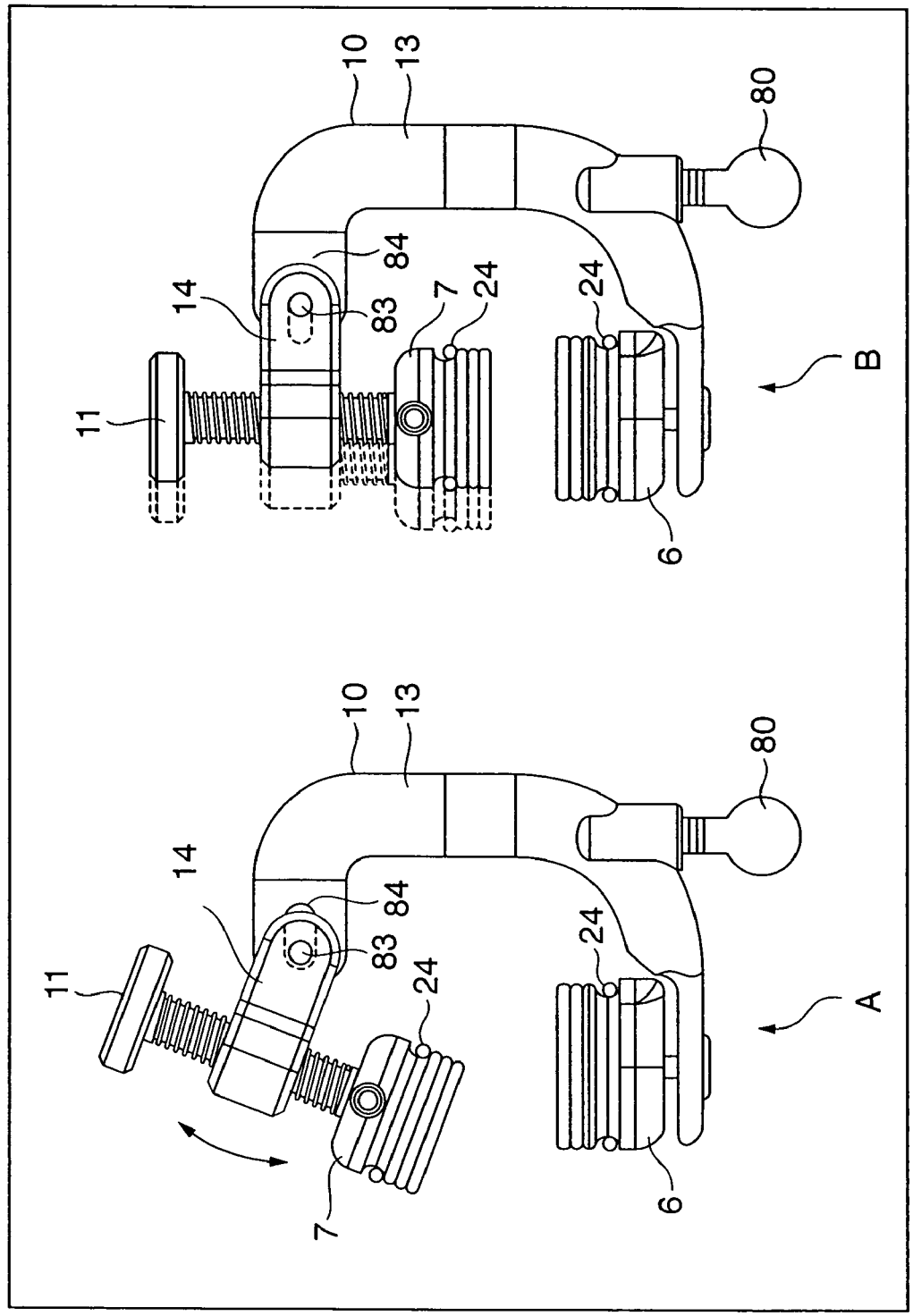
FIG. 6 is a view showing the state in which an outer cuff is open (A of FIG. 6) and the state in which the outer cuff is slid (B of FIG. 6) in the attaching portion 3.

Also, in the attaching portion 3 as shown in A of FIG. 6, the second holding member 14 pivots on an adjusting screw 83 of a holding member junction portion when the screw 83 is loosened. Accordingly, by tightening the adjusting screw 83 with the second holding member being set at an angle desired by the user, it is possible to change the state in which the outer cuff assembly 7 directly opposes the inner cuff assembly 6 (the head of the outer cuff assembly 7 is not turned) to a non-opposing state. Since the user can slightly change the positional relationship between the two cuff assemblies 6 and 7 in accordance with his or her taste in combination with the head turn structure (A of FIG. 6) of the outer cuff assembly 7, it is possible to more flexibly cope with an individual difference of the tragus 221. That is, the cuffs can be appropriately attached to tragi 221 having various shapes, so more appropriate blood pressure measurement is possible.

Furthermore, in the attaching portion 3 as shown in B of FIG. 6, when the adjusting screw 83 of the holding member junction portion is loosened, the second holding member 14 can slide in addition to the pivoting motion described above, so the relative positional relationship in the lateral direction between the inner cuff assembly 6 and outer cuff assembly 7 can be changed. This sliding motion is achieved by forming, in the second holding member 14, an elongated screw receiver 84 for receiving the adjusting screw 83. That is, the head of the adjusting screw 83 can slide to the right and left in the screw receiver 84 when the adjusting screw 83 is loosened, and is fixed to a position where the adjusting screw 83 is tightened. Note that a similar sliding mechanism or another sliding mechanism (e.g., a mechanism using a rail) may also be used to extend and contract, by a predetermined width, the end portion of the open end of the second holding member 14 on which the inner cuff assembly 6 is mounted. That is, the inner cuff assembly 6 and outer cuff assembly 7 need only be offset from the state (A of FIG. 5) in which they relatively directly oppose each other.

B of FIG. 6 shows the state in which the second holding member 14 is shortest (the dotted lines indicate the normal state shown in A of FIG. 5). When the attaching portion 3 is attached to the tragus 221 in this state, the inner cuff assembly 6 can be inserted into the ear hole to a position deeper than in the normal state. Accordingly, even when the person to be measured feels unstable or uncomfortable when the attaching portion 3 is attached in the normal lateral state (e.g., the state shown in A of FIG. 5), the attached state can be readily determined in accordance with the taste of the person to be measured (e.g., a patient) or the person who measures (e.g., a doctor).

In this embodiment as described above, the holding member 10 comprises the head turn structure, pivoting structure, and sliding structure of the outer cuff assembly 7. This makes it possible to achieve the attached state of the attaching portion 3, which is more appropriate for blood pressure measurement, and more comfortable for the person to be measured.

Figure 10:
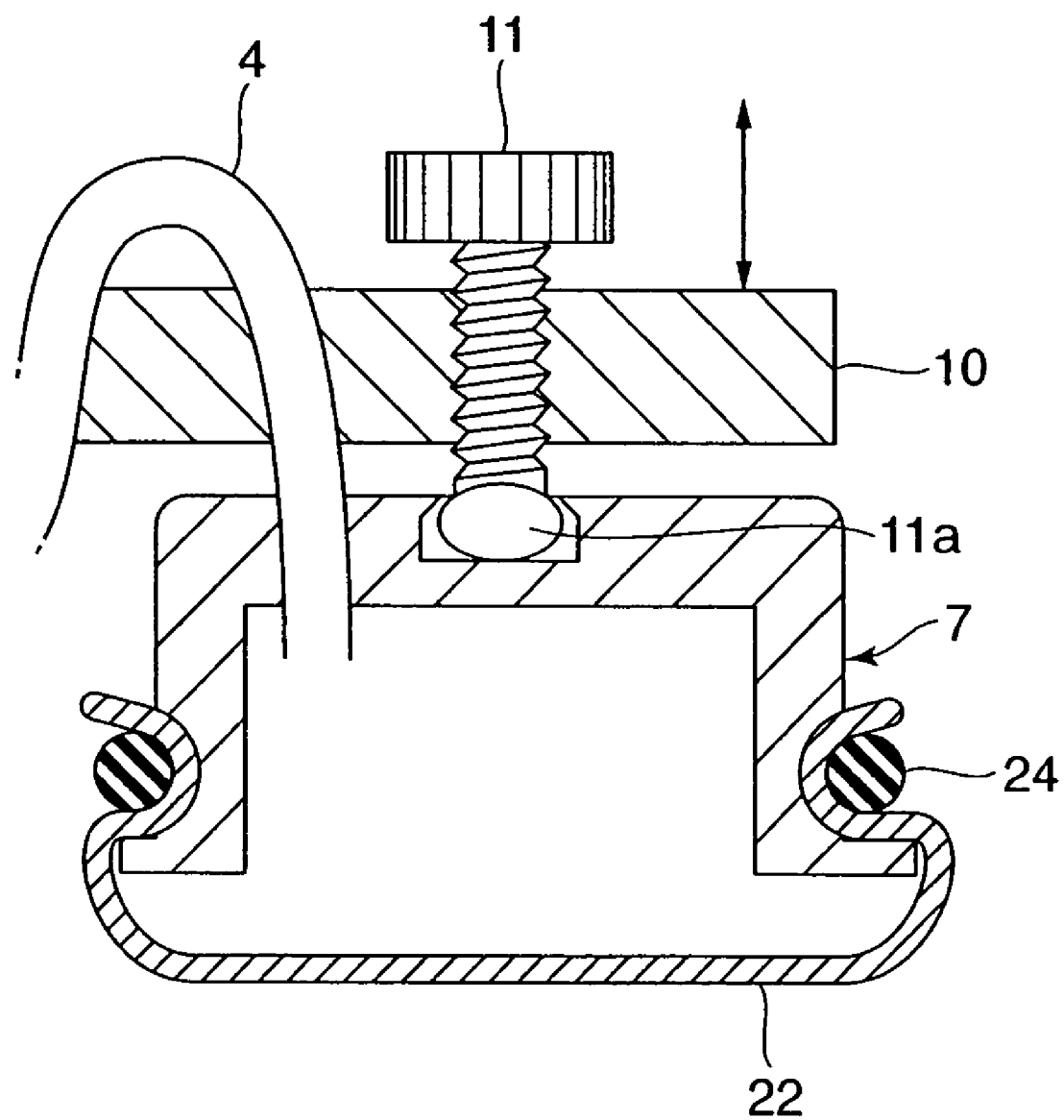
FIG. 10 is a view showing the case that the head turn structure is implemented by a ball bearing.

Also, a contact surface 25 of the outer cuff assembly 7 has a nearly circular shape. That is, a cuff portion (cuff bladder 22) forming a part of the outer cuff assembly 7 is almost circular when viewed from the upper surface, and the circumferential surface has, e.g., a two-step bellows structure (FIG. 10).

By contrast, a contact surface 25 of the inner cuff assembly 6 has a nearly elliptic shape. That is, a cuff portion (cuff bladder 23) forming a part of the inner cuff assembly 6 is almost elliptic when viewed from the upper surface, and the circumferential surface has, e.g., a two-step bellows structure (FIG. 12) similar to the cuff bladder 22 of the outer cuff assembly. Also, the direction of the major axis (large diameter) of the ellipse of the contact surface 25 matches the direction in which the inner cuff portion is inserted into the auricular concha cavity 227. This is so because the inner cuff portion can be smoothly inserted into the auricular concha cavity 227 when elongated along the insertion direction. In effect, an individual difference of the shape of the tragus 221 is very large, so an arrangement that facilitates insertion is very important. The circumferential surface of the cuff bladder 23 has a bellows structure (e.g., two-step bellows) as described above, and it is desirable to make the number of steps of the outer cuff bladder 22 equal to that of the inner cuff bladder 23. This is so when the balance between pressurization and depressurization is taken into consideration. Although the cuff sectional shape (contact surface shape) is an ellipse in this embodiment, it need only be an elongated shape, so an oval shape may also be used instead of an elliptic shape.

The arrangements of the cuff bladders 22 and 23 forming parts of the inner cuff assembly 6 and outer cuff assembly 7 will be described in more detail later with reference to FIGS. 10 to 13.

<Arrangements of Cuff Assemblies>

Figure 7:
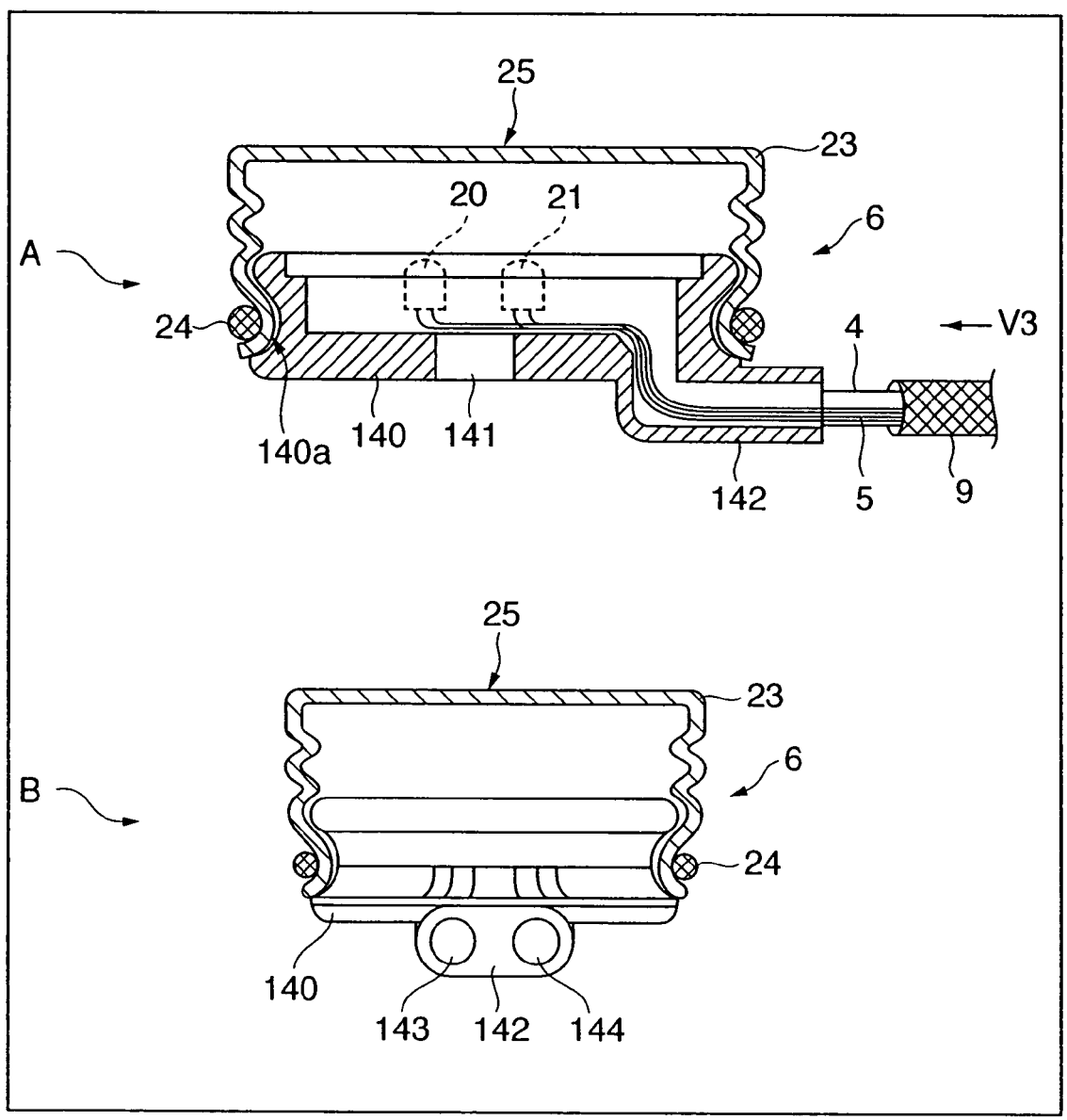
FIG. 7 is a view for explaining the structure of a cuff assembly.

A of FIG. 7 is a view showing the section of the completely assembled inner cuff assembly 6, and B of FIG. 7 is a view showing the section of the inner cuff assembly 6 viewed in a direction V3 in A of FIG. 7.

In the inner cuff assembly 6, an LED 20 as a light-emitting element and a phototransistor 21 as a light-receiving element for detecting a pulse wave signal are installed at predetermined positions (A of FIG. 7) in a cuff base 140. The cuff base 140 is covered with the cuff bladder 23, and the cuff bladder 23 is fixed to the position of a base recess 140a by an O-ring. Note that the cuff bladder 23 may also be adhered to the base recess 140a by an adhesive and then fixed by the O-ring. Note also that the phototransistor may also be installed in the outer cuff assembly 7 to detect a pulse wave signal by a transmitting method.

As shown in A of FIG. 7, the tube 4 and cables 5 are inserted into the cuff assembly 6 from an insertion portion 142. As shown in B of FIG. 7, the insertion portion 142 has two insertion holes 143 and 144. For example, the tube 4 is connected to the insertion hole 143, and the cables 5 are inserted into the insertion hole 145. The cables 5 are connected to the LED 20 and phototransistor 21 described above. After the tube 4 and cables 5 are inserted into the inner cuff assembly 6, the inner cuff assembly 6 is closed with a closing member (not shown) in order to prevent air leakage from the insertion portion 142, thereby creating a closed state in the inner cuff assembly 6. Note that the insertion portion 142 may also be closed with a chemical material such as an adhesive that solidifies when exposed to air, instead of the closing member.

The contact surface 25 of the inner cuff assembly 6 having the phototransistor as a light-receiving element has an elliptic shape or oval shape as will be described later, and the insertion portion 142 can be formed on either the major axis (large diameter) side or small diameter side of the ellipse. The contact surface 25 of the inner cuff assembly 6 is given an elliptic shape or oval shape by taking account of the ease with which the inner cuff assembly 6 is inserted into the auricular concha cavity 227. In this case, the easiness of insertion may improve if the tube 4 and cables 5 exist on the minor axis (small diameter) side rather than the large diameter side. This is so because when the inner cuff is inserted, the tube 4 and cables 5 may interfere with the tragus 221 to change the direction of the elliptic inner cuff assembly 6 (the cuff may rotate almost 90° from the state in which the large diameter is parallel to the insertion direction to the state in which the large diameter is perpendicular to the insertion direction).

Note that the arrangement of the outer cuff assembly 7 is the same as the inner cuff assembly 6 in that a cuff base is covered with the cuff bladder and the cuff bladder is fixed by an O-ring. In this embodiment, however, neither the LED 20 nor the phototransistor 21 is installed in the outer cuff assembly 7. In this case, the outer cuff assembly 7 has only one insertion hole 152 for the tube 4, unlike the inner cuff assembly 6. The LED 20 and phototransistor 21 may also be installed in the outer cuff assembly 7 as well. In this case, the outer cuff assembly 7 can have two insertion holes similar to the inner cuff assembly 6.

<Attachment of Outer Cuff Assembly 7: Head Turn Mechanism>

Figure 8:
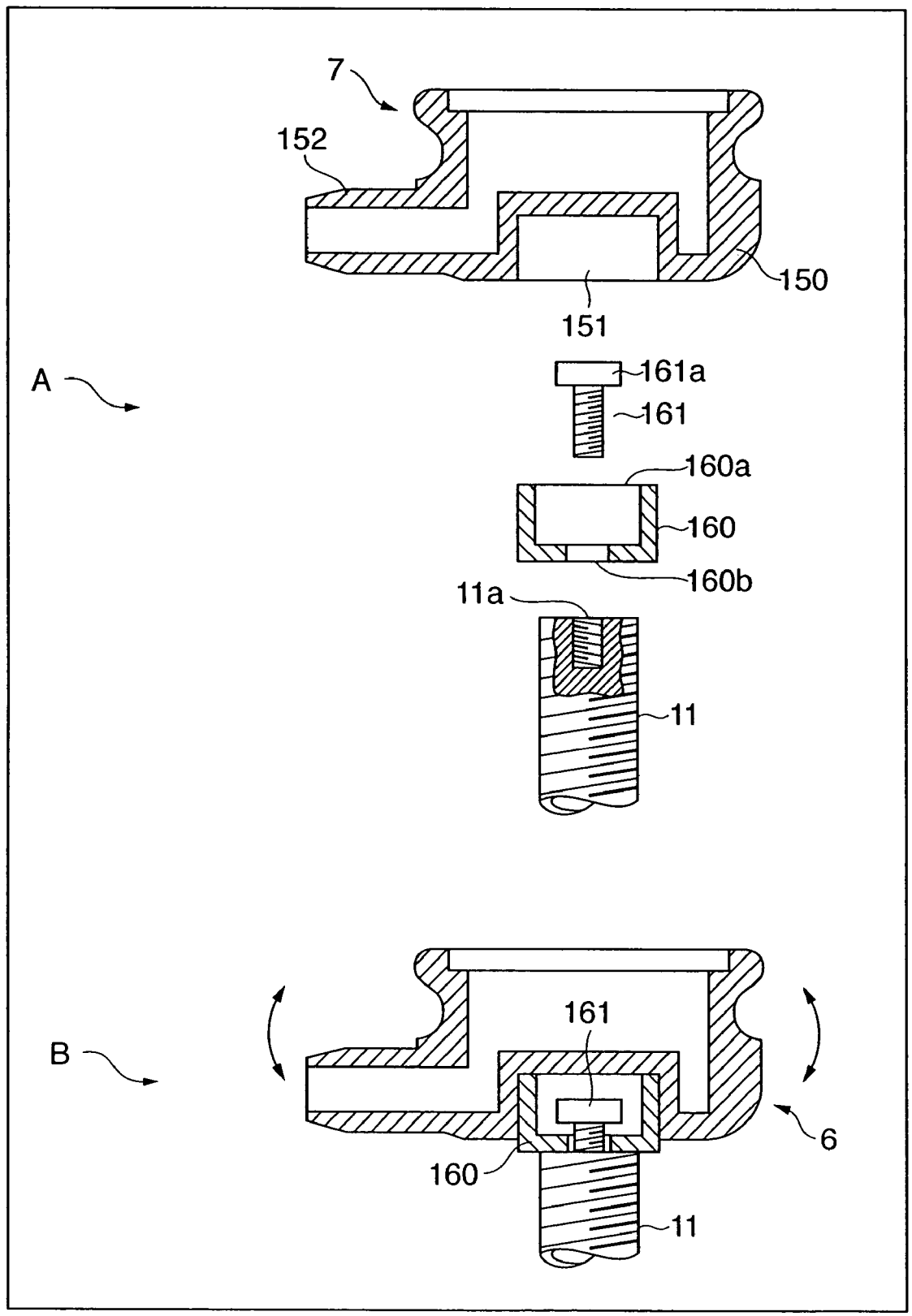
FIG. 8 is a view for explaining the head turn structure of the outer cuff.

FIG. 8 is a view for explaining the head turn mechanism of the outer cuff assembly 7. Referring to A of FIG. 8, an outer cuff base 150 has a press-fitting hole 151 into which a press-fitting member 160 is pressed, and the insertion hole 152 to which the tube 4 is connected.

The press-fitting member 160 has a cylindrical shape, an upper end 160a of the member is open, and an opening 160b having a size that allows a screw 161 to pass through is formed near the center of the bottom surface. The press-fitting member 160 is fixed to the clamping width adjusting screw 11 having a screw hole 11a by the screw 161. Since the length of the screw 161 is set larger than the depth of the screw hole 11a, it is possible to ensure a predetermined clearance between a screw head 161a of the screw 161 and the bottom surface of the press-fitting member 160.

After being attached to the clamping width adjusting screw 11 as described above, the press-fitting member 160 is pressed into the press-fitting hole 151 of the outer cuff assembly 6. Consequently, as shown in B of FIG. 8, the above-mentioned clearance allows the outer cuff assembly 7 to turn its head.

Figure 9:
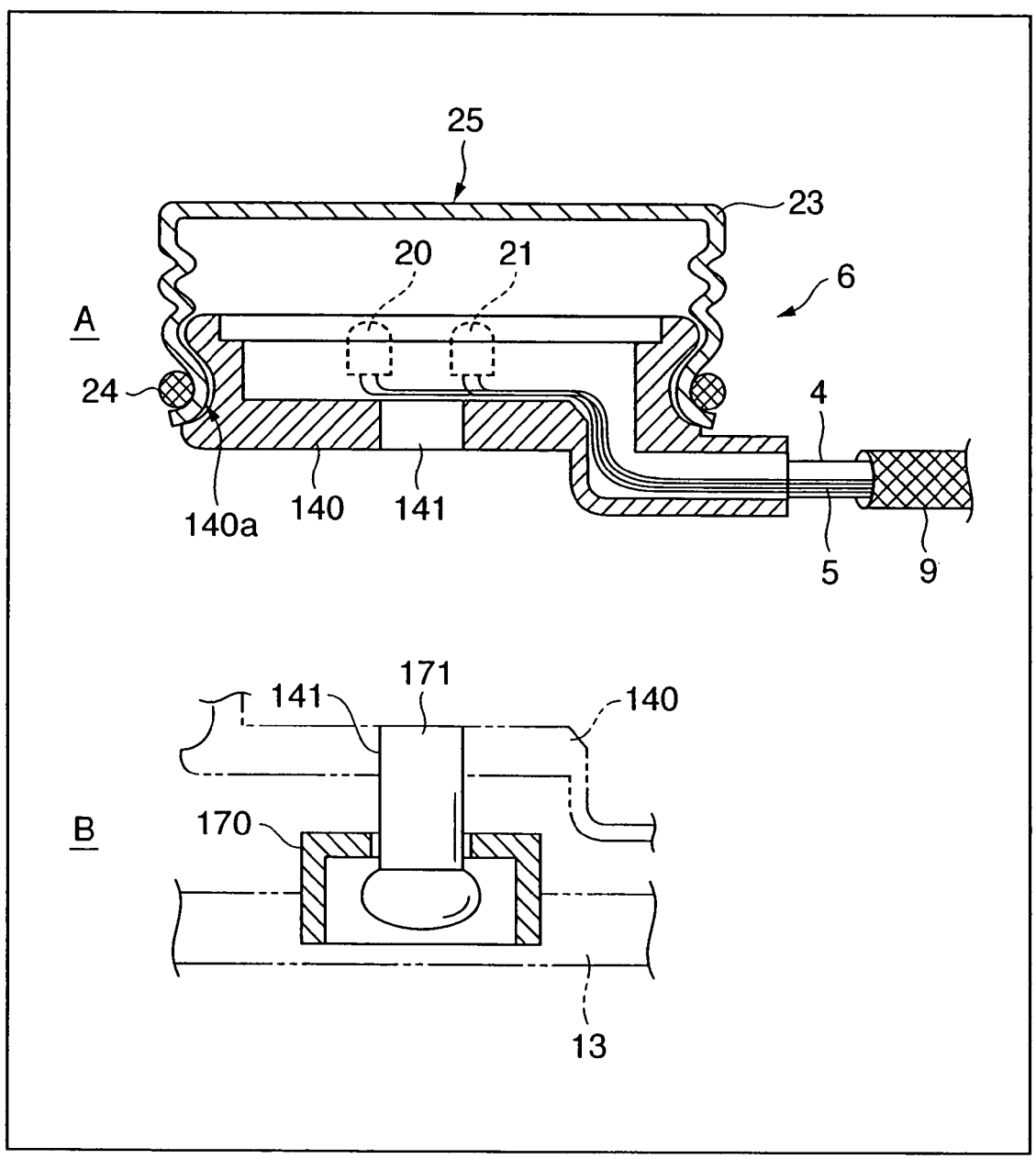
FIG. 9 is a view for explaining the head turn structure of an inner cuff.

The head turn mechanism of the inner cuff assembly 6 has a structure as shown in FIG. 9. Referring to B of FIG. 9, a press-fitting member 170 has a cylindrical shape, one end of the member is open, and an opening having a size that allows a press-fitting pin 171 to pass through is formed near the center of the other surface, similar to the press-fitting member 160 shown in FIG. 8. The press-fitting pin 171 is inserted into the opening of the press-fitting member 170, and pressed into a press-fitting hole 141 formed in the inner cuff base 140. In this manner, the press-fitting member 170 is fixed to the inner cuff base 140. In addition, the press-fitting member 170 is pressed, with its fully open end facing down, into a recess 172 formed in the end portion of the first holding member 13 forming the holding member 10. The inner cuff assembly 6 is attached to the first holding member as described above. Since the length of the press-fitting pin 171 is larger than the depth of the press-fitting hole 141, the inner cuff assembly 6 can move vertically and horizontally with a certain degree of freedom.

Although the above arrangement allows the cuff to turn its head, FIG. 10 shows another embodiment. In this case, as shown in FIG. 10, the head turn structure of the attaching portion 3 is implemented by axially fixing the outer cuff assembly 7 to the clamping width adjusting screw 11 by a ball bearing 11a. The head turn structure of the inner cuff assembly 6 may also be formed by a similar ball bearing.

<Arrangements of Cuff Bladders 22 and 23>

A of FIG. 11 is a plan view of the cuff bladder 22 forming a part of the outer cuff assembly 7, B of FIG. 11 is a front view of the cuff bladder 22, and C of FIG. 11 is a bottom view of the cuff bladder 22. FIG. 12 is a sectional view taken along a line X-X in A of FIG. 11.

Referring to FIG. 12, the cuff bladder 22 is integrally molded into a hat-like shape having a cylindrical portion 22b that elastically deforms between a pressurized state and depressurized state, and a lid portion 22a that extends from the cylindrical portion 22b and has the flat contact surface 25 that comes in contact with the tragus. The edge of an opening 28 is integrally molded as a flange portion 26. Also, the contact surface 25 can always come in contact with the tragus in a flat state because a first dimension t1 or the thickness of the lid portion 22a is set larger than a second dimension t2 or the thickness of the cylindrical portion 22b.

The lid portion 22a is formed into a circular shape, elliptic shape, or oval shape, the cylindrically portion 22b is similarly formed into a circular cylindrical shape, elliptic cylindrical shape, or oval cylindrical shape, and the cuff members are formed into shapes matching the cylindrical portion.

The cylindrical portion 22b is formed as a bellows member 27 having one or more steps, desirably, two steps. When the lid portion is circular, the diameter is set at 15 to 5 mm, desirably, about 8 mm, the first dimension t1 is set at 0.4 to 1 mm, desirably, about 0.6 mm, and the second dimension t2 is set at 0.1 to 0.8 mm, desirably, about 0.3 mm.

A of FIG. 13 is a plan view of the cuff bladder 23, B of FIG. 13 is a front view of the cuff bladder, C of FIG. 11 is a right side view of the cuff bladder, and D of FIG. 13 is a bottom view of the cuff bladder. A of FIG. 14 is a sectional view taken along a line X-X in A of FIG. 13, and B of FIG. 14 is a sectional view taken along a line Y-Y in A of FIG. 13.

Referring to FIGS. 13 and 14, when the lid portions of the cuff bladders 22 and 23 are elliptic or oval, the major axis dimension is 15 to 5 mm, desirably, about 10 mm, and the minor axis dimension is 10 to 4 mm, desirably, about 8 mm.

Also, in A of FIG. 14, the first dimension t1 is set at 0.4 to 1 mm, desirably, about 0.6 mm, and the second dimension t2 is set at 0.1 to 0.8 mm, desirably, about 0.3 mm.

Each of the cuff bladders 22 and 23 is integrally molded from an elastic material containing silicone rubber, natural rubber, or a predetermined synthetic resin and having a Shore hardness of 30 to 60, desirably, about 50.

As described above, in the hat-like cuff bladders 22 and 23 having the lid portion as the flat contact surface that comes in contact with the tragus 221, the first dimension t1 or the thickness of the lid portion is made larger than the second dimension t2 or the thickness of the cylindrical portion. At the time of pressurization, therefore, the contact surface 25 can move to the pressurization position while maintaining the flat state. Also, the contact surface 25 can move to the depressurization position while maintaining the flat state at the time of depressurization as well. Furthermore, the contact surface 25 can move almost parallel because the cylindrical portion of the cuff bladder has the bellows member (bellows structure) 27.

Note that since the circumferential surface of each of the cuff bladders 22 and 23 has the bellows structure as described above, it is possible to prevent the contact surface 25 of each of the cuff bladders 22 and 23 from expanding into a dome shape by the air pressure when the cuff is pressurized, thereby preventing the pressing force of the contact surface 25 from becoming nonuniform. That is, the bellows absorb an air pressure unnecessary to evenly press the tragus 221, and this makes it possible to maintain the contact surface 25 flat.

<Cuff Bladder in which Light-Shielding Layer is Formed>

When the LED element 20 and phototransistor 21 for optically detecting a pulse wave are incorporated into the cuff as described above, a portion of the cuff is exposed to the outside when the inner and outer cuffs are attached to the tragus. Under the influence of disturbance light, therefore, accurate blood pressure measurement becomes difficult to perform particularly when the user goes out and exposes himself or herself to direct sunlight although there is no serious problem indoors.

FIG. 15 shows printing steps of forming a light-shielding layer in the interior of the cuff bladder 22, together with a central sectional view of the cuff bladder 22.

Each of the cuff bladders 22 and 23 is integrally molded from a transparent or light-transmitting elastic material containing silicone rubber, natural rubber, or a predetermined synthetic resin and having a Shore hardness of 30 to 60, desirably, about 50. The cuff bladders 22 and 23 are each formed to be airtight with respect to the cuff members, and the contact surface 25 elastically deforms between the position of the pressurized state and the position of the depressurized state.

Disturbance light L enters the cuff bladders 22 and 23 because they are transparent, semitransparent, or light-transmitting. Therefore, when a high-sensitivity sensor is used under the sunlight, no accurate blood pressure measurement is possible due to the influence of the sunlight.

Accordingly, as shown in FIG. 15, in the cuff bladder 22 used in the inner cuff assembly 6, a light-shielding layer 45 for optically shielding portions except for an opening 46 is continuously formed to an inner wall surface 44 of the cylindrical portion. This makes it possible to irradiate only a blood pressure measurement portion with light by preventing the disturbance light L from entering the interior as shown in FIG. 15, and always detect an accurate pulse wave signal regardless of the location by receiving the reflected light, thereby measuring the blood pressure. Wear of the light-shielding layer 45 in use can be prevented by forming it in the interior as shown in FIG. 15, but it may also be formed outside if a wear resistance can be assured. Note that the light-shielding layer is formed in the outer cuff assembly 7 in order to detect a pulse wave signal by a light transmitting method by forming the phototransistor 21 in the interior of the outer cuff assembly 7.

When the lid portion 22 of the cuff bladder is formed into a circular shape as described above with reference to FIG. 11, the shape of the opening 46 of the light-shielding layer 45 is formed as a similar small circle. On the other hand, when the contact surface 25 is formed into an elliptic shape or oval shape as described above with reference to FIG. 13, the opening 46 of the light-shielding layer 45 is preferably formed into a circular shape or a similar small elliptic shape or oval shape.

When the contact surface 25 is a circle having a diameter (D1) of 15 to 5 mm, desirably, about 8 mm, the diameter of the opening 46 is set at 2 to 8 mm, desirably, about 5 mm. When the contact surface 25 is an ellipse or oval having a major axis dimension (D2) of 15 to 5 mm, desirably, about 10 mm and a minor axis dimension (D3) of 10 to 4 mm, desirably, about 8 mm, the opening 46 is formed into a circle having a diameter of 2 to 8 mm, desirably, about 5 mm, or into a circle, ellipse, or oval having an opening area equal to that of the circle. The light-shielding layer 45 having the opening 46 described above can be formed by, e.g., two-color injection molding.

In step S1 of FIG. 15, the outer appearances of the cuff bladders 22 molded by a rubber molding apparatus and deflashed are inspected to exclude defective products and select good products, and the good products are set on a coating tray (not shown). In step S2, degreasing is performed, no mixing of foreign matter is confirmed, and a masking sheet 70 having a shape and area corresponding to the opening 46 and including an adhesive surface having slight adhesion is adhered to the center of the back surface of the lid portion of the cuff bladder 22. In this step, a positioning jig is preferably used.

The foregoing is the preparation for coating of a silicone-based binder paint in which a pigment containing carbon black is mixed. Then, the process advances to step S3 to perform an ink coating step.

In this step, the light-shielding layer 45 indicated by the broken lines in FIG. 15 is formed by coating the binder paint by brushing or by using a spray gun. In this stage, the light-shielding layer is not well dried. In a room-temperature drying step in step S4, therefore, the cuff bladder is left to stand for about 1 hr to promote drying, and the masking 70 is removed by using a tool such as a forceps.

After that, the process advances to step S5, the dried cuff bladders are placed in an oven, and oven processing for baking coating is performed at about 200° C. for about 10 to 15 min. Then, the coating tray was removed outside from the oven. In a finish inspection step in step S6, outer appearance inspection is performed to inspect foreign matter, overflow of the paint to the opening 46, uneven coating, and the like, thereby selecting good products and terminating the process.

The cuff bladder 22 completed through the above steps is used as it is attached as shown in FIG. 7.

Note that although the foregoing are examples of the steps of forming the light-shielding layer inside the cuff bladder, almost similar steps can be used to form the light-shielding layer outside the cuff bladder. In addition, the two-color injection molding method described previously makes the coating step unnecessary, but a metal mold is complicated and expensive. Therefore, a method to be used will be determined in accordance with the number of cuffs to be manufactured.

<Another Example of Arrangement of Clamping Width Adjusting Mechanism Different from Clamping Width Adjusting Screw 11>

As described above, the clamping width adjusting screw 11 pivots forward and backward by threadably engaging the male screw portion formed on the outer circumferential surface of the main body of the adjusting screw 11 with the female screw hole formed in the second holding member 14. This allows the outer cuff assembly having the cuff bladder 23 to freely move and turn its head (FIGS. 8 to 10).

If the movement stroke of the outer cuff assembly is large, however, a short-tempered person or a person having trouble in fingers may think it troublesome to rotate the adjusting screw 11. Instead of the adjusting screw 11, therefore, it is also possible to use a brushing bush 49 that is a unidirectional moving member capable of moving to a desired position at once regardless of the length of the movement stroke of the outer cuff assembly.

That is, as shown in FIG. 16, the brushing bush 49 as a unidirectional moving member is obtained by integrally molding a plurality of elastically deformable flanges 49b on the outer circumferential surface and a ball bearing 49a at the end portion by using a predetermined nylon-based resin material. The diameter of the flange 49b is set larger than the inner diameter of a hole 15a formed in the other end of a third holding member 15. Accordingly, when the brushing bush 49 is inserted into the hole 15a in one direction indicated by the arrow, the three flanges 49b obliquely deform in the direction opposite to the insertion direction as shown in FIG. 16, and abut against the inner circumferential surface of the hole 15a by the elastic deformation force. The outer cuff assembly can be held in this state. Also, when the brushing bush 49 is pulled with a force larger than that for insertion, a stopper (not shown) abuts against the edge of the hole 15a to allow the brushing bush 49 to be pulled out to the original position. Note that the brushing bush 49 has an arrangement close to that of a product also called a one-touch fastener.

<Integrated Arrangement of Tube 4 and Cables 5>

Although the tube 4 and cables 5 are individually installed in FIG. 2, they may get entangled with each other when in use. Since a hollow portion serving as a channel for a fluid including air is formed along the longitudinal direction in the tube 4, it is possible to prevent the cables 5 from being exposed to the outside by passing them through this hollow portion. However, this arrangement requires a sealing portion for assuring airtightness in a portion where the cables 5 are pulled outside the tube 4, and makes it difficult to secure sealing properties because the tube 4 is freely bendable. This poses the problem of long-term durability, and also interferes with the assembling work.

Accordingly, various arrangements capable of improving the sealing properties and increasing the work efficient at the same time when integrating the tube 4 and cables 5 were examined.

As a result of this examination, it was concluded that, as in a perspective view of the outer appearance shown in FIG. 17, the best arrangement is to lay the cables 5 along the longitudinal direction on the outer circumferential surface of the tube 4, and cover the cables 5 and tube 4 with the covering member 9 having contraction and expansion properties, thereby integrating the cables 5 and tube 4.

More specifically, the cables 5 connected to the light-emitting element and light-receiving element described earlier are stranded conductors 5a and 5b connected from the light-emitting element and light-receiving element, the tube 4 is molded into a hollow shape as shown in FIG. 17 by using an elastic material containing silicone rubber, natural rubber, or a predetermined synthetic resin, and the covering member 9 is formed into a mesh from a fiber material having a predetermined yarn count. The covering member 9 undergoes a metal coating process for increasing the noise resistance, and covered with a cover (not shown).

When the tube 4 and cables 5 are thus integrated, they can be freely bent within the circle indicated by the alternate long and short dashed line in FIG. 17 when the user holds one end. In addition, no sealing member is necessary because the cables 5 can be directly extracted from the outer circumferential surface of the tube 4 as shown in FIG. 17. Also, when metal processing is performed on the covering member 9, the noise resistance can be further increased. Even when simply made of cloth, the covering member 9 has the function of protecting the tube 4 and cables 5 from the external environment, thereby making them difficult to damage.

As explained above, various problems arise when periodically measuring the blood pressure for every predetermined time by using the brachium or finger, so stable, highly accurate blood pressure measurement can be performed by using the tragus of the ear as a blood pressure measurement portion.

To continuously measure the blood pressure with high accuracy by a blood pressure measuring apparatus that uses the tragus as a blood pressure measurement portion as described above, pressurized air is supplied to each cuff by a battery-driven pressurizing pump. When the battery-driven pressurizing pump is used, however, long-term measurement is impossible because the battery rapidly exhausts, so a manual pressurizing pump may also be used. Various fluids can be used as a fluid medium to be pressurized. An example of a gas is air, and examples of a liquid are water, fats and oils including silicone oil, and alcohol. Any of these fluids can be appropriately selected.

<Arrangement of Connecting Portion>

FIG. 18 is a view showing the arrangement of the connecting portion 300 shown in FIG. 2. Referring to FIG. 18, the connecting portion 300 comprises an upper lid member 301 and accommodating member 302. The accommodating member 302 accommodates the tube 4 and cables 5. A tube plug 304 is attached to the end portion of the tube 4, and a female connector 305 is attached to the end portions of the cables 5. The female connector 305 is placed in a connector housing 309. The tube plug 304 is installed in a plug installation portion 311, and fixed to it from above by an E-ring 307. When the tube plug 304 is installed, a distal end portion having a predetermined length protrudes from a plug protrusion hole 308.

With the tube plug 304 and female connector 305 being installed, the upper lid member 301 is mounted on the accommodating member 302 from above. Consequently, upper lid locking portions 313a and 313b are respectively locked in accommodating portion locking holes 315a and 315b. With the locking portions 313 and locking holes 315 being locked, the upper lid member 301 and accommodating member 302 are tightly fixed by using a screw 306.

FIG. 19 is a view showing the way the connecting portion 300 is connected to the main body 2. Note that to allow easy understanding of the way of connection, FIG. 19 shows only the upper lid member 301 in the state before the connection, and only a part of the accommodating member 302 in the state after the connection.

As shown in FIG. 19, the press buttons 303 are fitted in the upper lid member 301 via springs 321. When connecting the connecting portion 300 to the main body 2, the width between the locking portions 322 is slightly decreased by pressing the press buttons 303. When the connecting portion 300 is inserted into a connecting recess of the main body 2, the female connector 305 is fitted on the male connector 318 of the main body 2, and the tube plug 304 is fitted in the tube plug hole 319. In addition, the locking portions 322 are locked in the locking holes 322 formed in the main body 2. In this manner, the connecting portion 300 and main body 2 are strongly fixed.

Also, after using the apparatus, the user can remove the connecting portion 300 by pulling it out from the connecting recess by unlocking the locking portions 322 from the locking holes 320 by pressing the press buttons 303.

Note that when fitting the connecting portion 300 to the main body 2, the locking portions 322 can be connected by pushing them into the connecting holes of the main body 2 without shortening the distance between them by pushing the press buttons 303, because they are leaf springs and have certain elasticity. However, to smoothly and safely connect the connecting portion 300 to the main body 2, it is favorable to more or less shorten the distance between the locking portions.

<Circuit Configuration of Photoelectric Volume Pulse Wave Sphygmomanometer>

FIG. 20 is a block diagram showing the configuration of an operating circuit 100 in the apparatus main body 2 when the blood pressure measuring apparatus is constructed as a photoelectric volume pulse wave sphygmomanometer. Referring to FIG. 20, the inner cuff (assembly) 6 of the attaching portion 3 to be attached to the tragus 221 incorporates the LED 20 as a light-emitting element and the phototransistor 21 as a light-receiving element forming a photoelectric sensor (pulse wave sensor). As described previously, the tube 4 is a rubber tube (air tube), and forms an air channel to the inner cuff 6. A pressure pump 108 has a small electric motor as a driving source, supplies compressed air to a condenser tank 107, and supplies pressurized air into the inner cuff assembly 6 after rectification. A rapid exhaust valve 104 branched from the tube 4 has a solenoid valve mechanism (not shown), and rapidly reduces the internal pressure of the inner cuff assembly 6. A slow exhaust valve 105 that is similarly branched reduces the internal pressure of the inner cuff assembly 6 at a predetermined rate (e.g., 2 to 3 mmHg/sec). Also, a pressure sensor 106 branched from the tube 4 changes an electrical parameter in accordance with the internal pressure of the cuff 6. A pressure detection amplifier (AMP) 107 connected to the pressure sensor 106 detects the electrical parameter of the pressure sensor 106, converts the parameter into an electrical signal, and amplifies the signal, thereby outputting an analog cuff pressure signal P.

The LED 20 irradiates a pulsing blood flow with light, and the phototransistor 21 detects the reflected light from the blood flow. A filter AMP 109 connected by the cables 5 is a pulse wave detection amplifier, and outputs an analog pulse wave signal M by amplifying the output signal from the phototransistor 21. The cables 5 connect the LED 20 to a light amount controller 118 that automatically changes the light amount, and connect the pulse wave detection amplifier 109 to a gain controller 119a that automatically changes the gain, and a time constant controller 119b that changes the time constant of a filter amplifier (not shown) forming the pulse wave detection filter amplifier 109. Also, an A/D converter (A/D) 110 connected as shown in FIG. 20 converts the analog signals M and P into digital data D.

A controller (CPU) 111 performs main control of the photoelectric volume pulse wave sphygmomanometer. The CPU 111 has an adjusted pressure register 111a that stores an adjusted pressure. Details of this control will be explained later with reference to flowcharts shown in FIGS. 22A and 22B and an operating waveform diagram shown in FIG. 23.

A ROM 112 contains a control program (to be described later) executed by the CPU 111. A RAM 113 includes a data memory, image memory, and the like. A liquid crystal display (LCD) 114 displays the contents of the image memory. An operation unit 116 is operated by the user to, e.g., input a measurement start command or set an adjusted pressure value. A buzzer 115 notifies the user that, e.g., the apparatus has sensed pressing of a key in the operation unit 116, or the measurement is complete. Note that the adjusted pressure register 111a is allocated in the CPU 111 in this embodiment, but an adjusted pressure storage unit may also be allocated in the RAM 113.

A dot matrix type display panel is used as the display panel 114 of the LCD, so the display panel 114 can display various kinds of information (e.g., characters, figures, and signal waveforms). The operation panel 116 has a measurement start switch (ST) and keys for inputting, e.g., a cuff pressure value. The apparatus further includes a power supply unit 121 having an exchangeable buttery, and a power switch (not shown).

Furthermore, the apparatus main body 2 has an external communication unit to be connected to a connector or cell phone (neither is shown). By connecting this external communication unit to a personal computer, it is possible to exchange various kinds of data with and save the blood pressure measurement results in an operation control parameter setting unit, data clear unit, and data saving unit of the personal computer.

FIG. 21 is a view showing the layout of the parts of the apparatus main body 2 shown in FIG. 2, in which the lid is removed from the apparatus main body 2. In FIG. 21, the same reference numerals as above denote the already explained arrangements or parts, and a repetitive explanation will be omitted. The apparatus main body 2 has a length of about 120 mm, a width of about 80 mm, a thickness of 27 mm, and an overall weight of 180 g. Since the apparatus main body 2 is thus made as compact and light as possible, it does not interfere with everyday life even when the user always carries it.

Also, the electronic parts that perform the various kinds of control described above are mounted on a substrate 140 having a packaging area that occupies the internal space. On the other hand, the pressure pump 108, condenser tank 107, slow exhaust valve 105, and rapid exhaust valve 104 are connected to the tube 4 that is formed integrally with these components as described above, and have the relative positional relationship as shown in FIG. 21, so these components can be installed together with the power supply unit 121 containing four exchangeable AAA cells. The electronic parts are thus arranged such that the limited internal space can be effectively used. In addition, a chargeable secondary battery that can be repetitively used or commercially available AAA cells that are readily obtainable can be simply exchanged by opening and closing a lid (not shown).

<Operation of Photoelectric Volume Pulse Wave Sphygmomanometer>

The operation of the blood pressure measuring apparatus according to this embodiment as a photoelectric volume pulse wave sphygmomanometer will be explained below. FIGS. 22A and 22B are flowcharts for explaining the measurement process of the blood pressure measuring apparatus (photoelectric volume pulse wave sphygmomanometer). Referring to FIGS. 23A and 23B, when the user turns on the power supply by the power switch of the apparatus, an initial self-diagnosing process (not shown) is first performed to set the initial values of the apparatus. After that, the process is started when the user presses the measurement start switch.

The cuff pressure P is read in step S101, and whether the residual pressure of a cuff 1 is equal to or smaller than a prescribed value is determined in step S102. If the residual pressure exceeds the prescribed value, the LCD 114 displays "residual pressure error" in step S123. If the residual pressure is equal to or smaller than the prescribed value, the user sets a cuff pressurization value (e.g., a value larger than a maximum blood pressure value of 120 to 210 mmHg) in step S103 by using the operation unit 118, and sets the light amount and gain at predetermined values in step S104.

After the pressurization value, light amount, and gain are set, the rapid exhaust valve 104 and slow exhaust valve 105 are closed in steps S105 and S106. In step S107, the pressure pump 3 is driven to start pressurization (raising the pressure). This is the start of a measurement process upon pressurization, and the cuff pressure starts increasing at a constant rate (e.g., 2 to 3 mmHg/sec). In step S108, the individual functional blocks perform data processing, and measure the minimum blood pressure and maximum blood pressure. When the maximum blood pressure is measured (S109), the driving of the pressure pump 103 is stopped in step S112.

In step S110, whether the cuff pressure is higher than a pressurization value U set in step S103. If P$\leq$U, the cuff pressure still falls within a normal measurement range, so the measurement continues. If P>U, the cuff pressure is higher than the set value, so the LCD 114 displays "measurement error" in step S111. If necessary, the LCD 114 additionally displays detailed information such as "signal abnormality upon pressurization". In step S113, it is determined whether the signal level of a pulse wave signal obtained upon pressurization falls within a predetermined range over which highly accurate blood pressure measurement is possible. If the signal level falls within the predetermined range, the LCD 114 displays the measured maximum blood pressure value and minimum blood pressure value in step S120, and a tone signal is supplied to the buzzer 115 in step S121.

If the signal level falls outside the predetermined range in step S113, the light amount and gain are adjusted on the basis of the signal level of the pulse wave signal in step S114. In step S114, the apparatus performs, e.g., the following processing. If the carrier wave of the pulse wave is equal to or smaller than a standard value (20% to 40% of the full scale of the A/D converter 110), whether the step light amount is a maximum is checked. If the step light amount is not a maximum, the light amount is increased by controlling the light amount controller 118. If the light amount is a maximum, the gain is raised. On the other hand, if the carrier wave level is equal to or larger than the standard value, whether the gain is a minimum is checked. If the gain is not a minimum, the gain controller 119a lowers the gain by feedback control. If the gain is a minimum, the light amount is decreased.

When the adjustment of the light amount and gain is complete, the slow exhaust valve 105 is opened in step S115. This is the start of a measurement process upon depressurization (pressure reduction), and the cuff pressure starts reducing at a constant rate (e.g., 2 to 3 mmHg/sec). In step S116, the individual functional blocks perform data processing, and measure the maximum blood pressure and minimum blood pressure. In step S117, whether the minimum blood pressure value is detected upon depressurization is determined. If no value is detected, the measurement continues. In step S118, whether the cuff pressure is lower than a predetermined value L (e.g., 40 mmHg) is determined. If P$\geq$L, the cuff pressure still falls within the normal measurement range, so the process returns to step S116. If P<L, the cuff pressure is lower than the normal measurement range, so the LCD 114 displays "measurement error" in step S119. If necessary, the LCD 114 additionally displays detailed information such as "signal abnormality upon depressurization".

If it is determined in step S117 that the measurement is complete, this means that the measurement process is complete within the normal measurement range. Accordingly, the LCD 14 displays the measured maximum blood pressure value and minimum blood pressure value in step S120, and a tone signal is supplied to the buzzer 115 in step S121. Preferably, different tone signals are supplied for normal termination and abnormal termination. In step S122, the remaining air in the cuff 6 is rapidly exhausted, and the start of the next measurement is waited for.

<Blood Pressure Calculations>

FIG. 23 is a graph showing the correlation between the cuff pressure and pulse wave signal. FIG. 23 shows waveforms during a time period from the start of the measurement upon pressurization (step S108) to the end of the measurement upon depressurization (step S116).

Referring to FIG. 23, blood pressure measurements are generally performed as follows. That is, in the measurement upon pressurization, the cuff pressure at the point (a) at which the pulse wave signal starts changing its magnitude is the minimum blood pressure, and the cuff pressure at the point (b) at which the pulse wave signal disappears is the maximum blood pressure. On the other hand, the blood pressure measurement upon depressurization is opposite to that upon pressurization; the cuff pressure at the point (c) at which the pulse wave signal appears is the maximum blood pressure, and the cuff pressure at the point (d) at which the pulse wave signal stops changing its magnitude is the minimum blood pressure.

Note that this embodiment has disclosed an example in which the reflected light from the blood in the blood vessel is detected, but it is also possible to detect transmitted light instead.

As explained above, the photoelectric volume pulse wave sphygmomanometer of this embodiment makes it possible to provide a photoelectric volume pulse wave sphygmomanometer capable of highly accurate measurement by adjusting the signal level of a pulse wave signal such that the signal level falls within a predetermined standard range, and also capable of reducing the physical burden on the user caused by the cuff pressure by shortening the blood pressure measurement time. Note that the tragus and its periphery are less sensible to pain, so it is also possible to effectively reduce the pain caused by the cuff pressure. This further achieves the effect of facilitating the application of the apparatus to continuous blood pressure measurement.

Note that the above blood pressure measuring apparatus detects the pulse wave by using the light-emitting element 20 and light-receiving element 21, but it is also possible to detect the pulse wave by sensing the pulsation of the blood vessel on the surface of a living body as a pressure change by using a cuff that applies a pressure to the tragus. That is, a cuff to which a pressure is applied converts the pulsation obtained from a living body into a pressure change in the cuff, and a pressure sensor senses this pressure change in the cuff. This arrangement can also detect the pulse wave of a living body. It is also possible to install a miniature microphone in a cuff portion in contact with a living body, detect Korotkoff sounds generated when the cuff presses a portion of the living body, and measure the blood pressure on the basis of the generation or disappearance of Korotkoff sounds equal to higher than a predetermined level.

OTHER EMBODIMENTS

In the above embodiment, as shown in FIG. 20, only one (the interior of the inner cuff assembly 6) of the pair of cuffs having the arrangement that clamps the tragus 221 has the irradiating portion (LED 20) that irradiates the blood flow in the blood vessel with light, and the light-receiving portion (phototransistor 21) that detects the reflected light from the blood flow.

FIG. 24 is a block diagram showing an example of the arrangement of a blood pressure measuring apparatus according to another embodiment as a photoelectric volume pulse wave sphygmomanometer. In FIG. 24, the same reference numerals as above denote the already explained arrangements or parts, and a repetitive explanation will be omitted. An inner cuff assembly 6 and outer assembly 7 for clamping a tragus 221 respectively incorporate LEDs 20a and 20b as light-emitting portions and phototransistors 21a and 21b as light-receiving portions that detect reflected light.

As described above, it is also possible to arrange sensors in both the inner and outer cuffs, and simultaneously measure the blood pressures on the back side and front side of the tragus. In this arrangement, one cuff can press the blood vessel (arteriole) on the back side of the external ear and its periphery, and the other cuff can press the superficial temporal artery or its branched blood vessel on the front side of the external ear and its periphery.

FIG. 25 is a graph showing the results of blood pressure measurements performed by simultaneous measurements using the inner and outer cuffs. As shown in FIG. 25, as a pressurization curve W1 decreases, a pulse wave signal K1 of the inner cuff 6 changes, and a pulse wave signal K2 of the outer cuff 7 changes. As shown in FIG. 25, the amplitude of the pulse wave signal K1 starts largely changing earlier than the waveform of the pulse wave signal K2. The maximum blood pressure and minimum blood pressure can be measured more accurately by using both the thus changing pulse wave signals.

Note that the blood pressure in the external ear and its periphery (more specifically, the tragus and its periphery) is measured for the following reason as well.

That is, the blood vessel (arteriole) in the tragus and its periphery is close to the blood vessels in the brain, so it is presumably possible to measure the change in blood pressure resulting from the brain. On the other hand, in the tragus and its periphery, the artery (superficial temporal artery) that directly connects to the heart exists in addition to the blood vessel (arteriole) existing in the cartilage (primarily the tragus) of the ear. In the tragus and its periphery, therefore, a small apparatus can simultaneously measure the blood pressures having different kinds of information (i.e., the blood pressure resulting from the brain and the blood pressure resulting from the heart). The photoelectric volume pulse wave sphygmomanometer of this embodiment can set the signal level of the pulse wave signal within the predetermined standard range, and can accurately measure the blood pressure in the external ear and its periphery. At the same time, it is possible to shorten the blood pressure measurement time, thereby reducing the physical burden on the user caused by the cuff pressure.

The present invention is not limited to the above embodiments, and various changes and modifications can be made without departing from the spirit and scope of the invention. Therefore, to apprise the public of the scope of the present invention, the following claims are made.

The invention claimed is:

1. A blood pressure measuring apparatus comprising:
   an inner cuff to be inserted into an ear hole, and an outer cuff to be positioned outside a tragus;
   holding means for holding said inner cuff and said outer cuff;
   pulse wave detecting means incorporated into at least one of said inner cuff and said outer cuff to detect a pulse wave signal obtained by light from blood flowing through a blood vessel;
   pressurizing/depressurizing means for pressurizing and depressurizing said inner cuff and said outer cuff by using a fluid, after said inner cuff and said outer cuff clamp the tragus;
   a tube connected from said inner cuff and said outer cuff to said pressurizing/depressurizing means to supply the fluid;
   pressure detecting means connected to said tube to detect pressures of said inner cuff and said outer cuff; and
   blood pressure measurement control means for measuring a blood pressure value from the pulse wave signal, wherein said inner cuff and said outer cuff oppose each other, and a thickness of a lid portion of each of said inner cuff and said outer cuff is made larger than a thickness of a cylindrical portion.

2. A blood pressure measuring apparatus according to claim 1, wherein one end of said holding means is open, end portions of said holding means where said inner cuff and said outer cuff are arranged are substantially parallel, and and an auxiliary member adapted to be in contact with a predetermined position of an ear of a person to be measured and increases attachment stability of said inner cuff and said outer cuff at the tragus is attached to said holding means.

3. A blood pressure measuring apparatus according to claim 2, wherein said auxiliary member protrudes from said holding means, and a length of the protrusion from said holding means is adjustable by a protrusion length adjusting mechanism.

4. A blood pressure measuring apparatus according to claim 1, further comprising an ear hook which has a tube holding portion which holds the tube connected to said inner cuff and said outer cuff, and adapted to guide said tube to said pressurizing!depressurizing means through a back of the ear of the person to be measured.

5. A blood pressure measuring apparatus according to claim 4, wherein said ear hook and said holding means are independent members except for portions integrated via said tube.

6. A blood pressure measuring apparatus according to claim 4, wherein said ear hook has a shape portion adapted to press at least an anti-helix of the ear of the person to be measured.

7. A blood pressure measuring apparatus according to claim 4, wherein a stopper member which regulates a length to be pulled in a predetermined direction is attached to said tube.

8. A blood pressure measuring apparatus according to claim 7, wherein said tube holding portion of said ear hook has a plurality of Lube holding portions, and said stopper member is attached to a position of a tube holding portion closest to said holding means.

9. A blood pressure measuring apparatus according to claim 1, wherein said holding means includes a first holding member which holds said outer cuff and a second holding member which holds said inner cuff, said first holding member is pivotally connected to said second holding member, and when said first holding member is in a steady position without pivoting, said first holding member and an end portion of said second holding member at which said inner cuff is placed are substantially parallel to each other in said holding means.

10. A blood pressure measuring apparatus according to claim 1, further comprising a clamping width adjusting mechanism which adjusts a clamping width between said outer cuff and said inner cuff.

11. A blood pressure measuring apparatus according to claim 1, wherein a head turn mechanism attaches at least one of said outer cuff and said inner cuff to said holding means.

12. A blood pressure measuring apparatus according to claim 1, wherein a circumferential surface of each of said outer cuff and said inner cuff, except for a contact surface adapted to be in direct contact with the tragus, is formed into bellows.

13. A blood pressure measuring apparatus according to claim 12, wherein a numbers of steps of said bellows of said outer cuff and said inner cuff are the same.

14. A blood pressure measuring apparatus according to claim 1, wherein sectional shapes of said outer cuff and said inner cuff are different 15. A blood pressure measuring apparatus according to claim 1, wherein a sectional shape of said outer cuff is substantially a circle, and a sectional shape of said inner cuff is substantially one of an ellipse and an oval.

16. A blood pressure measuring apparatus according to claim 1, wherein the at least one of said inner cuff and said outer cuff into which is incorporated the pulse wave detecting means has a light-shielding layer which prevents disturbance light.

* * * * *